United States Patent [19]

Paoletti et al.

[11] Patent Number: 5,759,841
[45] Date of Patent: *Jun. 2, 1998

[54] IMMUNOLOGICAL COMPOSITION OF MEASLES VIRUS UTILIZING RECOMBINANT POXVIRUS

[75] Inventors: Enzo Paoletti, Delmar; Jill Taylor, Albany, both of N.Y.

[73] Assignee: Virogenetics Corporation, Troy, N.Y.

[*] Notice: The term of this patent shall not extend beyond the expiration date of Pat. Nos. 5,494,807, and 5,503,834.

[21] Appl. No.: 487,412

[22] Filed: Jun. 7, 1995

Related U.S. Application Data

[63] Continuation-in-part of Ser. No. 26,217, Mar. 1, 1993, Pat. No. 5,335,673, Ser. No. 36,218, Mar. 24, 1993, abandoned, and Ser. No. 847,951, Mar. 6, 1992, abandoned, and a division of Ser. No. 73,962, Jun. 8, 1993, Pat. No. 5,503,834, which is a continuation of Ser. No. 776,867, Oct. 22, 1991, abandoned, which is a continuation-in-part of Ser. No. 621,614, Nov. 30, 1990, abandoned, said Ser. No. 847,951, is a continuation-in-part of Ser. No. 666,056, Mar. 7, 1991, abandoned, said Ser. No. 36,218, Mar. 24, 1993, abandoned, is a continuation of Ser. No. 713,967, Jun. 11, 1991, abandoned, which is a continuation-in-part of Ser. No. 666,056, Mar. 7, 1991, abandoned, said Ser. No. 26,217, is a continuation of Ser. No. 666,056, Mar. 7, 1991, abandoned.

[51] Int. Cl.$^6$ .................. C12N 7/00; C12N 15/00; A61K 39/12; A61K 39/155
[52] U.S. Cl. ............ 435/235.1; 435/320.1; 435/172.3; 424/199.1; 424/211.1; 424/212.1; 424/232.1; 530/350
[58] Field of Search .................. 435/235.1, 172.3, 435/320.1; 530/350; 424/199.1, 211.1, 212.1, 232.1

[56] References Cited

U.S. PATENT DOCUMENTS

| | | | |
|---|---|---|---|
| 5,180,675 | 1/1993 | Drillien et al. | 435/235.1 |
| 5,364,773 | 11/1994 | Paoletti et al. | 435/69.1 |
| 5,503,834 | 4/1996 | Paoletti et al. | 424/199.1 |

FOREIGN PATENT DOCUMENTS

| | | | |
|---|---|---|---|
| 314569 | 5/1989 | European Pat. Off. | |
| 8903429 | 4/1989 | WIPO | C12P 21/00 |

OTHER PUBLICATIONS

Norrby et al, 1986, J. Virology, vol. 58, pp. 536–541.
DeVries et al, 1988, J. Gen. Virology, vol. 69 pp. 2071–2083.
Barrett et al, 1987, Virus Research, vol. 8, pp. 373–386.
Adams, J.M., and D.T. Imagawa, Proc. Soc. Exper. Biol. Med. 96, 240–244 (1957).
Albrecht, P., K. Herrman, and G.R. Burns, J. Virol. Methods 3, 251–260 (1981).
Alkhatib, G., and D. Briedis, Virology 150, 479–490 (1986).
Alkhatib, G., C. Richardson, and S–H. Shen, Virology 175, 262–270 (1990).
Appel, M.J.G., and O.R. Jones, Proc. Soc. Exp. Biol. Med. 126, 571–574 (1967).
Appel, M.J.G., and D.S. Robson, Am. J. Vet. Res. 34, 1459–1463 (1973).
Avery, R.J., and J. Niven, Infect. Immun. 26, 795–801 (1979).
Baker, J.A., B.E. Sheffy, D.S. Robson, J. Gilmartin, Cornell Vet (USA) 56, 588–594 (1966).
Bertholet, C., R. Drillien, and R. Wittek, Proc. Natl. Acad. Sci. USA 82, 2096–2100 (1985).
Bestetti, G., R. Fatzer, and R. Frankhauser, Acta Neuropathol. 43, 69–75 (1978).
Black, F.L., L.L. Berman, M. Libel, C.A. Reichelt, F. de P. Pinheiro, A.T. da Rosa, F. Figuera, and E.S. Gonzales, Bull. W.H.O. 62, 315–319 (1984).
Bush, M., R.J. Montali, D. Brownstein, A.E. James, Jr., and M.J.G. Appel, J. Am. Vet. Med. Assoc. 169, 959–960 (1976).
Carpenter, J.W., M.J.G. Appel, R.C. Erickson, and M.N. Novilla, J. Am. Vet. Med. Assoc. 169, 961–964 (1976).
Choppin, P.W., C.D. Richardson, D.C. Merz, W.W. Hall, and A. Scheid, J. Infect. Dis. 143, 352–363 (1981).
Clewell, D.B., J. Bacteriol. 110, 667–676 (1972).
Clewell, D.B., and D.R. Helinski, Proc. Natl. Acad. Sci. USA 62, 1159–1166 (1969).
Colinas, R.J., R.C. Condit, and E. Paoletti, Virus Research 18, 49–70 (1990).
DeLay, P.D., S.S. Stone, D.T. Karzon, S. Katz, and J. Enders, Am. J. Vet. Res. 26, 1359–1373 (1965).
Diallo, A., Vet. Micro. 23, 155–163 (1990).
Dowling, P.C., B.M. Blumberg, J. Menonna, J.E. Adamus, P. Cook, J.C. Crowley, D. Kolakofsky, and S.D. Cook, J. Gen. Virol. 67, 1987–1992 (1986).
Drillien, R., D. Spehner, A. Kirn, P. Giraudon, R. Buckland, F. Wild, and J.P. Lecocq, Proc. Natl. Acad. Sci. USA 85, 1252–1256 (1988).
Engelke, D.R., P.A. Hoener, and F.S. Collins, Proc. Natl. Acad. Sci. USA 85, 544–548 (1988).
Fenner, F., P.A. Bachmann, E.P.J. Gibbs, F.A. Murphy, M.J. Studdert, and D.O. White, In Veterinary Virology, ed. F. Fenner, (Academic Press, Inc., New York) pp. 485–503 (1987).

(List continued on next page.)

*Primary Examiner*—Marian C. Knode
*Assistant Examiner*—Ali R. Salimi
*Attorney, Agent, or Firm*—Frommer, Lawrence & Haug LLP; William S. Frommer; Thomas J. Kowalski

[57] ABSTRACT

What is described is a recombinant poxvirus, such as vaccinia virus or canarypox virus, containing foreign DNA from Morbillivirus. In one embodiment, the foreign DNA is expressed in a host by the production of a measles virus glycoprotein. In another embodiment, the foreign DNA is expressed in a host by the production of at least two measles virus glycoproteins. What is also described is a vaccine containing the recombinant poxvirus for inducing an immunological response in a host animal inoculated with the vaccine. By the present invention, cross-protection of dogs against canine distemper is obtained by inoculating the dog with the recombinant poxvirus.

42 Claims, 17 Drawing Sheets

OTHER PUBLICATIONS

Gillespie, J.H., and D.T. Karzon, Proc. Soc. Exp. Biol Med. 105, 547–551 (1960).

Giraudon, P., Ch. Gerald, and T.F. Wild, Intervirology 21, 110–120 (1984).

Goebel, S.J., G.P. Johnson, M.E. Perkus, S.W. Davis, J.P. Winslow, and E. Paoletti, Virology 179, 247–266 (1990a).

Goebel, S.J., G.P. Johnson, M.E. Perkus, S.W. Davis, J.P. Winslow, and E. Paoletti, Virology 179, 517–563 (1990b).

Graves, M.C., S.M. Silver, and P.W. Choppin, Virology 86, 254–263 (1978).

Guo, P., S. Goebel, S. Davis, M.E. Perkus, B. Languet, P. Desmettre, G. Allen, and E. Paoletti, J. Virol. 63, 4189–4198 (1989).

Guo, P., S. Goebel, S. Davis, M.E. Perkus, J. Taylor, E. Norton, G. Allen, B. Languet, P. Desmettre, and E. Paoletti, J. Virol. 64, 2399–2406 (1990).

Hall, W.W., R.A. Lamb, and P.W. Choppin, Virology 100, 433–449 (1980).

Hartley, W.J., Vet. Path. 11, 301–312 (1974).

Imagawa, D.T., P. Goret, and J.M. Adams, Proc. Natl. Acad. Sci. USA 46, 1119–1123 (1960).

Karzon, D.T., Pediatrics 16, 809–818 (1955).

Karzon, D.T., Annals of the N.Y. Academy of Sci. 101, 527–539 (1962). Kazacos, K.R., H.L. Thacker, H.L. Shivaprasad, and P.P. Burger, J. Am. Vet. Med. Assoc. 179, 1166–1169 (1981).

Kingsbury, D.W., M.A. Bratt, P.W. Choppin, R.P. Hanson, T. Hosaka, V. ter Meulen, E. Norrby, W. Plowright, R. Rott, and W.H. Wunner, Intervirology 10, 137–152 (1978).

Kunkel, T.A., Proc. Natl. Acad. Sci. USA 82, 488–492 (1985).

Lennon, J.L., and F.L. Black, J. Ped. 108, 671–676 (1986).

Mandecki, W., Proc. Natl. Acad. Sci. USA 83, 7177–7181 (1982).

Mandecki, W., Proc. Natl. Acad. Sci. USA 83, 7177–7181 (1986).

Maniatis, T., E.F. Fritsch, and J. Sambrook, Molecular Cloning, Cold Spring Harbor Laboratory, NY 545 pages (1982).

Maniatis, T., E.F. Fritsch, and J. Sambrook, Molecular Cloning, Cold Spring Harbor Laboratory, NY 545 pages (1986).

Merz, D.C., A. Schied, and P. Choppin, J. Exp. Med. 151, 275–288 (1980).

Moura, R.A., and J. Warren, J. Bact. 82, 702–705 (1961).

Norrby, E., and Y. Gollmar, Infect. Immun. 11, 231–239 (1975).

Norrby, E., G. Enders–Ruckle, and V. ter Meulen, J. Infect. Dis. 132, 262–269 (1975).

Norrby, E., S.N. Chen, T. Togashi, H. Shesberadaran, and K.P. Johnson, Archives of Virology 71, 1–11 (1982).

Norrby, E., and M.N. Oxman, In Fields Virology 2nd Ed., B.N. Fields and D.M. Knipe, eds. (Raven Press, NY) pp. 1013–1044 (1990).

Novick, S.L. and D. Hoekstra, Proc. Natl. Acad. Sci. USA 85, 7433–7437 (1988).

Orvell, C., and E. Norrby, J. Gen. Virol. 50, 231–245 (1980).

Panicali, D., and E. Paoletti, Proc. Natl. Acad. Sci. USA 79, 4927–4931 (1982).

Paterson, R.G., and R.A. Lamb, Cell 48, 441–452 (1987).

Perkus, M.E., A. Piccini, B.R. Lipinskas, and E. Paoletti, Science 229, 981–984 (1985).

Perkus, M.E., K. Limbach, and E. Paoletti, J. Virol. 63, 3829–3836 (1989).

Perkus, M.E., S.J. Goebel, S.W. Davis, G.P Johnson, K. Limbach, E.K. Norton, and E. Paoletti, Virology 179, 276–286 (1990).

Phillips, T.R., J.L. Jensen, M.J. Rubino, W.C. Yang, and R.D. Schultz, Can. J. Vet. Res. 53, 154–160 (1989).

Piccini, A., M.E. Perkus, and E. Paoletti, In Methods in Enzymology, vol. 153, eds. Wu, R., and Grossman, L., (Academic Press) pp. 545–563 (1987).

Preblud, S.R., and S.L. Katz, In Vaccines, eds. S.A. Plotkin and E.A. Mortimer, (W.B. Saunders Co.) pp. 182–222 (1988).

Richardson, C.D., A. Berkovich, S. Rozenblatt, and W. Bellini, J. Virol. 54, 186–193 (1985).

Richardson, C., D. Hull, P. Greer, K. Hasel, A. Berkovich, G. Englund, W. Bellini, B. Rima, and R. Lazzarini, Virology 155, 508–523 (1986).

Roberts, J.A., J. Immunol. 94, 622–628 (1965).

Rosel, J.L., P.L. Earl, J.P. Weir, and B. Moss, J. Virol. 60, 436–449 (1986).

Sanger, F., S. Nicklen, and A.R. Coulson, Proc. Natl. Acad. Sci. USA 74, 5463–5467 (1977).

Shapira, S.K., J. Chou, F.V. Richaud, and M.J. Casadaban, Gene 25, 71–82 (1983).

Spehner, D., R. Drillien, and J.P. Lecocq, J. Virol. 64, 527–533 (1990).

Stephenson, J.R. and V. ter Meulen, Proc. Nat. Acad. Sci. USA 76, 6601–6605 (1979).

Tabor, S., and C.C. Richardson, Proc. Natl. Acad. Sci. USA 84, 4767–4771 (1987).

Taylor, J., R. Weinberg, Y. Kawaoka, R.G. Webster, and E. Paoletti, Vaccine 6, 504–508 (1988a).

Taylor, J., R. Weinberg, B. Languet, P. Desmettre, and E. Paoletti, Vaccine 6, 497–503 (1988b).

Taylor, J., C. Edbauer, A. Rey–Senelonge, J.F. Bouquet, E. Norton, S. Goebel, P. Desmettre, and E. Paoletti, J. Virol. 64, 1441–1450 (1990).

Taylor, J., S. Pincus, J. Tartaglia, C. Richardson, G. Alkhatib, D. Briedis, M. Appel, E. Norton, and E. Paoletti, J. Virol. 65, 4263–4272 (1991).

Tizard, I., J. Am. Vet. Med. Assoc. 196, 1851–1858 (1990).

Vialard, J., M. Lalumiere, T. Vernet, D. Briedis, G. Alkhatib, D. Henning, D. Levin, and C. Richardson, J. Virol. 64, 37–50 (1990).

Warren, J., M.K. Nadel, E. Slater, and S.J. Millian, Amer. J. Vet. Res. 21, 111–119 (1960).

Wild, T.F., E. Malvoisin, and R. Buckland, J. Gen. Virol. 72, 439–442 (1991).

Wild, F., P. Giraudon, D. Spehner, R. Drillien, and J–P. Lecocq, Vaccine 8, 441–442 (1990).

Norrby, E. et al. 1986 J. Virol. vol. 58, pp. 536–541.

DeVries, P. et al. 1988 J. Gen. Virol vol. 69, 2071–2083.

Barrett, T. et al. 1987 Virus Research vol. 8 pp. 373–386.

Yuen, L., and B. Moss, Proc. Natl. Acad. Sci. USA 84, 6417–6421 (1987).

1

IMMUNOLOGICAL COMPOSITION OF MEASLES VIRUS UTILIZING RECOMBINANT POXVIRUS

CROSS REFERENCE TO RELATED APPLICATIONS

This application is a division of U.S. application Ser. No. 08/073,962, filed Jun. 8, 1993, now U.S. Pat. No. 5,503,834, which in turn is a continuation of 07/776,867 filed Oct. 22, 1991, now abandoned, which in turn is a continuation-in-part of 07/621,614 filed Nov. 30, 1990, now abandoned. This application is also a continuation-in-part of U.S. application Ser. No. 07/847,951 filed Mar. 6, 1992, now abandoned, which in turn is a continuation-in-part of U.S. application Ser. 07/666,056 filed Mar. 7, 1991, also now abandoned. This application is also a continuation-in-part of U.S. application Ser. No. 08/036,218 filed Mar. 24, 1993, now abandoned, which is a continuation of U.S. application Ser. No. 07/713,967 filed Jun. 11, 1991, now abandoned, which in turn is a continuation-in-part of U.S. application Ser. No. 07/066,056 filed Mar. 7, 1991, now abandoned. This application is also a continuation-in-part of U.S. application Ser. No. 08/026,217 filed Mar. 1, 1993, now U.S. Pat. No. 5,335,67, which is a continuation of U.S. application Ser. No. 07/666,056 filed Mar. 7, 1991, now abandoned.

FIELD OF THE INVENTION

The present invention relates to a modified poxvirus and to methods of making and using the same. More in particular, the invention relates to recombinant poxvirus, which virus expresses gene products of a Morbillivirus gene, and to vaccines which provide protective immunity against Morbillivirus infections.

Several publications are referenced in this application by arabic numerals within parentheses. Full citation to these references is found at the end of the specification immediately preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Canine distemper virus (CDV) and measles virus (MV) are members of the Morbillivirus subgroup of the family Paramyxovirus genus (Diallo, 1990; Kingsbury et al., 1978). The viruses contain a non-segmented single-stranded RNA genome of negative polarity. Canine distemper is a highly infectious febrile disease of dogs and other carnivores. The mortality rate is high; ranging between 30 and 80 percent. Dogs surviving often have permanent central nervous system damage (Fenner, et al., 1987). Similarly, measles virus causes an acute infectious febrile disease characterized by a generalized macropapular eruption. The disease mainly affects children.

The characteristics of Morbilliviruses have recently been reviewed by Norrby and Oxman (1990) and Diallo (1990). As reported for other Paramyxoviruses (Avery and Niven, 1979; Merz et al., 1980) two structural proteins are crucial for the induction of a protective immune response. These are the membrane glycoprotein hemagglutinin (HA), which is responsible for hemagglutination and attachment of the virus to the host cell, and the fusion glycoprotein (F), which causes membrane fusion between the virus and the infected cell or between the infected and adjacent uninfected cells (Graves et al., 1978). The order of genes in the MV genome has been deduced by Richardson et al. (1985) and Dowling et al. (1986). The nucleotide sequence of the MVHA gene and MVF gene has been determined by Alkhatib and Briedis (1986) and Richardson et al. (1986), respectively.

CDV and MV are structurally similar and share a close serological relationship. Immunoprecipitation studies have shown that antiserum to MV will precipitate all CDV proteins (P, NP, F, HA and M). By contrast, antiserum to CDV will precipitate all MV proteins except the HA glycoprotein (Hall et al., 1980; Orvell et al., 1980; Stephenson, et al., 1979). In light of this close serological relationship, it has previously been demonstrated that vaccination with MV will elicit protection against CDV challenge in dogs (Gillespie et al., 1960; Moura et al., 1961; Warren et al., 1960). Neutralizing antibodies against CDV have been reported in human anti-MV sera (Adams et al., 1957; Imagawa et al., 1960; Karzon, 1955; Karzon, 1962) but neutralizing antibodies against MV have not been found in anti-CDV sera from dogs (Delay et al., 1965; Xarzon, 1962; Roberts, 1965).

MV HA and F genes have been expressed in several viral vectors including vaccinia virus (Drillien et al., 1988; Wild et al., 1991), fowlpox virus (Spehner et al., 1990; Wild et al., 1990), adenovirus (Alkhatib et al., 1990) and baculovirus (Vialard et al., 1990). In these studies, authentic MV proteins were expressed which were functional in hemagglutination (Vialard et al., 1990) hemolysis (Alkhatib et al., 1990; Vialard et al., 1990) or cell fusion (Alkhatib et al., 1990; Vialard et al., 1990; Wild et al., 1991) assays. When inserted into a vaccinia virus vector, the expression of either the HA or the F protein was capable of eliciting a protective immune response in mice against MV encephalitis (Drillien et al., 1988). Similarly, expression of the F protein in a fowlpox virus vector elicited protective immunity against MV encephalitis in mice (Wild et al., 1990). No protection studies were reported with other vectors.

European Patent Application No. 0 314 569 relates to the expression of an MV gene in fowlpox.

Perkus et al. (1990) recently described the definition of two unique host range genes in vaccinia virus. These genes encode host range functions which permit vaccinia virus replication on various cell substrates in vitro. The genes encode host range functions for vaccinia virus replication on human cells as well as cells of rabbit and porcine origin. Definition of these genes provides for the development of a vaccinia virus vector, which, while still expressing foreign genes of interest, would be severely restricted in its ability to replicate in defined cells. This would greatly enhance the safety features of vaccinia virus recombinants.

An attenuated vector has been developed by the sequential deletion of six non-essential regions from the Copenhagen strain of vaccinia virus. These regions are known to encode proteins that may have a role in viral virulence. The regions deleted are the tk gene, the hemorrhagic gene, the A-type inclusion gene, the hemagglutinin gene and the gene encoding the large subunit of the ribonucleotide reductase as well as the C7L through K1L sequences defined previously (Perkus et al., 1990). The sequences and genomic locations of these genes in the Copenhagen strain of vaccinia virus have been defined previously (Goebel et al., 1990 a,b). The resulting attenuated vaccinia strain is designated as NYVAC.

The technology of generating vaccinia virus recombinants has recently been extended to other members of the poxvirus family which have a more restricted host range. The avipoxvirus, fowlpox, has been engineered as a recombinant virus expressing the rabies G gene (Taylor et al., 1988b). This recombinant virus is also described in PCT Publication No. WO89/03429. On inoculation of the recombinant into a number of nonlavian species an immune response to rabies is elicited which in mice, cats and dogs is protective against a lethal rabies challenge.

Both canine distemper and measles are currently controlled by the use of live attenuated vaccines (Fenner et al., 1987; Preblud et al., 1988). Immunization is recommended for control of CDV using a live attenuated vaccine at eight weeks of age and again at 12 to 16 weeks of age. Although immunity to CDV is life-long, because of the highly infectious nature of the agent and the severity of the disease, annual revaccination is usually recommended.

One problem with the current policy of continual revaccination is that CDV immune mothers pass neutralizing antibody to offspring in the colostrum. It is difficult to ascertain when these antibody levels will wane such that pups can be vaccinated. This leaves a window when pups may be susceptible to CDV infection. Use of a recombinant vaccine expressing only the measles virus glycoproteins may provide a means to overcome the inhibitory effects of maternal antibody and allow vaccination of newborns. In fact, it has been demonstrated that CDV-specific antibodies in pups that suckled CDV immune mothers did not prevent the development of MV-specific antibodies when inoculated with a MV vaccine (Baker et al., 1966).

Other limitations of the commonly used modified live CDV vaccines have been previously documented (Tizard, 1990) and are linked to the ability of these vaccine strains to replicate within the vaccinated animals. These deleterious effects are most notable when the CDV vaccine strain is co-inoculated with canine adenovirus 1 and 2 into dogs resulting in immunosuppression, thrombocytopenia, and encephalitis (Bestetti et al., 1978; Hartley, 1974; Phillips et al., 1989). The modified live CDV vaccines have also been shown to induce distemper in other animal species including foxes, Kinkajous, ferrets, and the panda (Bush et al., 1976; Carpenter et al., 1976; Kazacos et al., 1981). Therefore, the use of a recombinant CDV vaccine candidate would eliminate the continual introduction of modified live CDV into the environment and potential vaccine-associated and vaccine-induced complications which have arisen with the use of the conventional CDV vaccines.

The use of poxvirus vectors may also provide a means of overcoming the documented inhibitory effect that maternal antibody has on vaccination with presently utilized live attenuated CDV strains in dogs. Pups born to mothers previously immunized at a young age with a poxvirus recombinant may avoid the interference of CDV-specific maternal antibody. Additionally, the ability of both vaccinia virus and canarypox virus vectors harboring MV HA and F genes to elicit these responses and the lack of serological cross-reactivity between the two poxviruses provides a further advantage in that one vector could be utilized early in the pup's life and the other later, to boost CDV-specific immunity. This would eliminate the release of live attenuated CDV strains into the environment; an event linked to the occurrence of vaccine-induced and vaccine-associated complications (Tizard, 1990).

It can thus be appreciated that provision of a Morbillivirus recombinant poxvirus, and of vaccines which provide protective immunity against Morbillivirus infections, would be a highly desirable advance over the current state of technology.

OBJECTS OF THE INVENTION

It is therefore an object of this invention to provide recombinant poxviruses, which viruses express gene products of Morbilliviruses, and to provide a method of making such recombinant poxviruses.

It is an additional object of this invention to provide for the cloning and expression of Morbillivirus coding sequences, particularly measles virus coding sequences, in a poxvirus vector, particularly vaccinia virus or canarypox virus vectors.

It is another object of this invention to provide a vaccine which is capable of eliciting Morbillivirus neutralizing antibodies, hemagglutination-inhibiting antibodies and protective immunity against Morbillivirus infection and a lethal Morbillivirus challenge, particularly providing cross-protection of dogs against canine distemper using a measles virus recombinant poxvirus vaccine.

These and other objects and advantages of the present invention will become more readily apparent after consideration of the following.

STATEMENT OF THE INVENTION

In one aspect, the present invention relates to a recombinant poxvirus containing therein a DNA sequence from Morbillivirus in a nonessential region of the poxvirus genome. The poxvirus is advantageously a vaccinia virus or an avipox virus, such as canarypox virus. The Morbillivirus is advantageously measles virus.

According to the present invention, the recombinant poxvirus expresses gene products of the foreign Morbillivirus gene. In particular, the foreign DNA codes for a measles virus glycoprotein, advantageously measles virus hemagglutinin glycoprotein and measles virus fusion glycoprotein. Advantageously, a plurality of measles virus glycoproteins are co-expressed in the host by the recombinant poxvirus.

In another aspect, the present invention relates to a vaccine for inducing an immunological response in a host animal inoculated with the vaccine, said vaccine including a carrier and a recombinant poxvirus containing, in a nonessential region thereof, DNA from Morbillivirus, particularly measles virus. Advantageously, the DNA codes for and expresses a measles virus glycoprotein, particularly measles virus hemagglutinin glycoprotein and measles virus fusion glycoprotein. A plurality of measles virus glycoproteins advantageously are co-expressed in the host. The poxvirus used in the vaccine according to the present invention is advantageously a vaccinia virus or an avipox virus, such as canarypox virus.

BRIEF DESCRIPTION OF THE DRAWINGS

A better understanding of the present invention will be had by referring to the accompanying drawings, in which.

DETAILED DESCRIPTION OF THE INVENTION

Figure 1A:
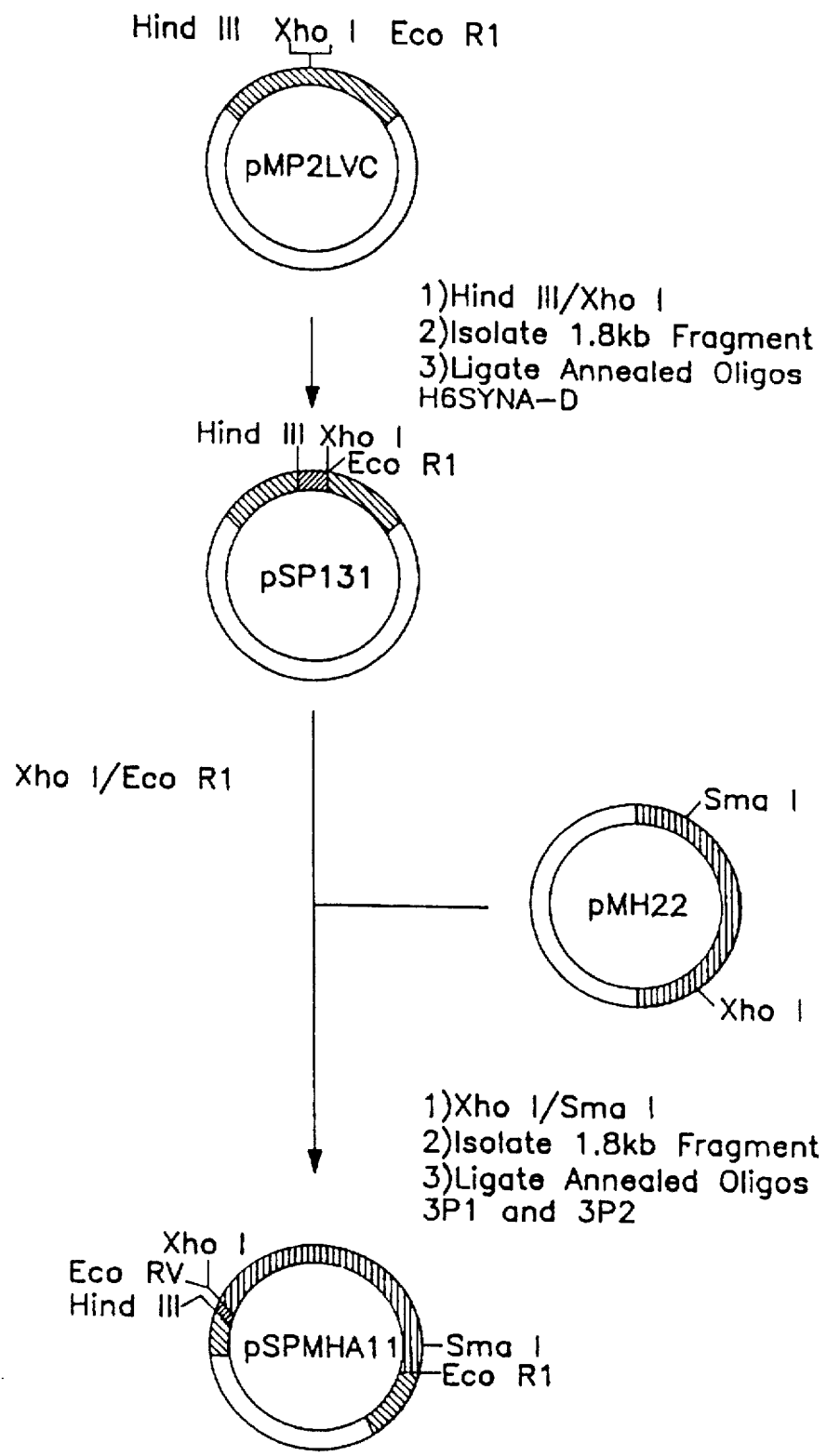
FIG. 1 schematically shows a method for the construction of plasmid pSPM2LHAVC used to derive recombinant vaccinia virus vP557 expressing the MV hemagglutinin gene.
Figure 1B:
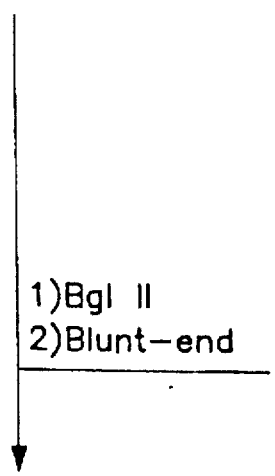
Figure 1B:
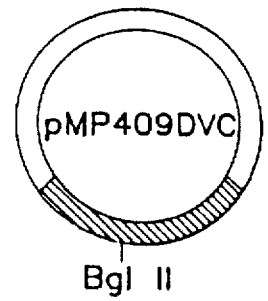
Figure 1B:
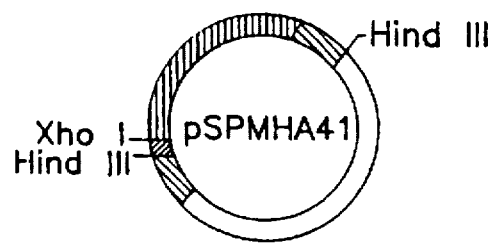
Figure 1B:
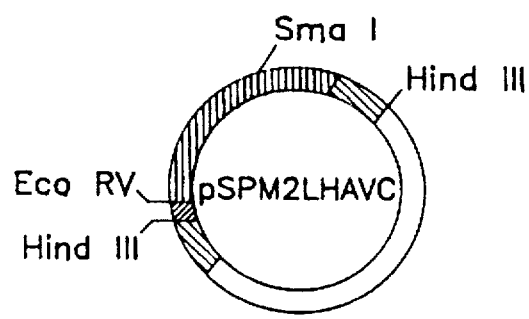

A better understanding of the present invention and of its many advantages will be had from the following examples, given by way of illustration.

EXAMPLE 1

Generation of Vaccinia Virus Recombinants Containing the Measles Hemagglutinin Gene The rescuing virus used in the production of both recombinants was the Copenhagen strain of vaccinia virus from which the thymidine kinase gene had been deleted. All viruses were grown and titered on VERO cell monolayers.

The early/late vaccinia virus H6 promoter (Rosel et al., 1986; Taylor et al., 1988a,b) was constructed by annealing four overlapping oligonucleotides, H6SYN A–D. The resultant H6 sequence is as follows:

Vaccinia Virus H6 Promoter (SEQ ID NO:1/SEQ ID NO:2):

HindIII

5' AGCTTCTTTATTCTATACTTAAAAAGTGAAAATAAATACAAAGGTTCTTGAGGGTTGT
    AGAAATAAGATATGAATTTTTCACTTTTATTTATGTTTCCAAGAACTCCCAACA

GTTAAATTGAAAGCGAGAAATAATCATAAATTATTTCATTATCGCGATATCCGTTAAGTT
CAATTTAACTTTCGCTCTTTATTAGTATTTAATAAAGTAATAGCGCTATAGGCAATTCAA

TGTATCGTAC-3'
ACATAGCATGAGCT-5'

XhoI

Referring now to FIG. 1, the annealed H6SYN oligonucleotides were ligated into pMP2LVC digested with XhoI/HindIII to yield plasmid pSP131. The plasmid pMP2LVC contains the leftmost 0.4 kbp of the vaccinia virus (Copenhagen strain) HindIII K region within pUC18. The construction of pMP2LVC was performed as follows: a 0.4 kbp HindIII/SalI fragment from the HindIII K region was isolated and blunt-ended with the Klenow fragment of the E. coli DNA polymerase in the presence of 2 mM dNTPs. This fragment was inserted into pUC18 which had been digested with PvuII. The resulting plasmid was designated pMP2VC. The plasmid pMP2VC was linearized with SspI. Synthetic oligonucleotides MPSYN52 (SEQ ID NO:3) (5'-ATTATTTTTATAAGCTTGGATCCCTCGAGGGTACCC-CCGGGGAGCTCGAATTCT-3') and MPSYN53 (SEQ ID NO:4) (5'-AGAATTCGAGCTCCCCGGGGGTACCCTCGAGGGA-TCCAAGCTTATAAAAATAAT-3') were annealed and inserted into the leftmost of the two SspI sites located within the vaccinia virus sequences. The resultant plasmid pMP2LVC contains a multiple cloning region in the intergenic region between the K1L and K2L open reading frames.

Annealed oligonucleotides 3P1 (SEQ ID NO:5) (5'-GGGAAGATGGAACCAATCGCAGATAG-3') and 3P2 (SEQ ID NO:6) (5'-AATTCTATCTGCGATTGGGGTTCCATCTTCCC-3') containing the extreme 3' sequences of the HA gene and a sticky EcoRI end were ligated to a 1.8 kbp XhoI/SmaI fragment from pMH22 containing the remainder of the HA gene and pSP131 digested with XhoI and EcoRI. The resultant plasmid was designated pSPMHA11. The plasmid pMH22 was derived from a full length cDNA clone of the measles HA gene by creating a XhoI site at the ATG initiation codon (Alkhatib et al., 1986).

A 1.9 kbp HindIII/EcoRI fragment from pSPMHA11, containing the measles HA gene, was isolated and blunt-ended with the Klenow fragment of the E. coli DNA polymerase in the presence of 2 mM dNTPs. The isolated fragment was inserted into pMP409DVC (Guo et al., 1989) digested with BglII and blunt-ended by treatment with mung bean nuclease. Insertion into this vector yielded plasmid pSPMHA41. The XhoI site between the H6 promoter and the initiation codon of the HA gene was removed by oligonucleotide directed double strand break mutagenesis (Mahdecki, 1982) using oligonucleotide HAXHOD (SEQ ID NO:7) (5'-ATATCCGTTAAGTTTGTATCG-TAATGTCACCACAACGAGACCGGAT-3'). Plasmid pSPM2LHAVC was generated by this procedure. Insertion plasmid pSPM2LHAVC was used in in vitro recombination experiments with vaccinia virus vP458 as the rescue virus to generate recombinant vP557. vP458 contains the E. coli lac Z gene in the M2L insertion site of vP410. This vaccinia virus recombinant contains the measles HA gene in the M2L locus of the genome, replacing the lac Z gene.

EXAMPLE 2

Generation of Vaccinia Virus Recombinants Containing the Measles Fusion Gene

Figure 2A:
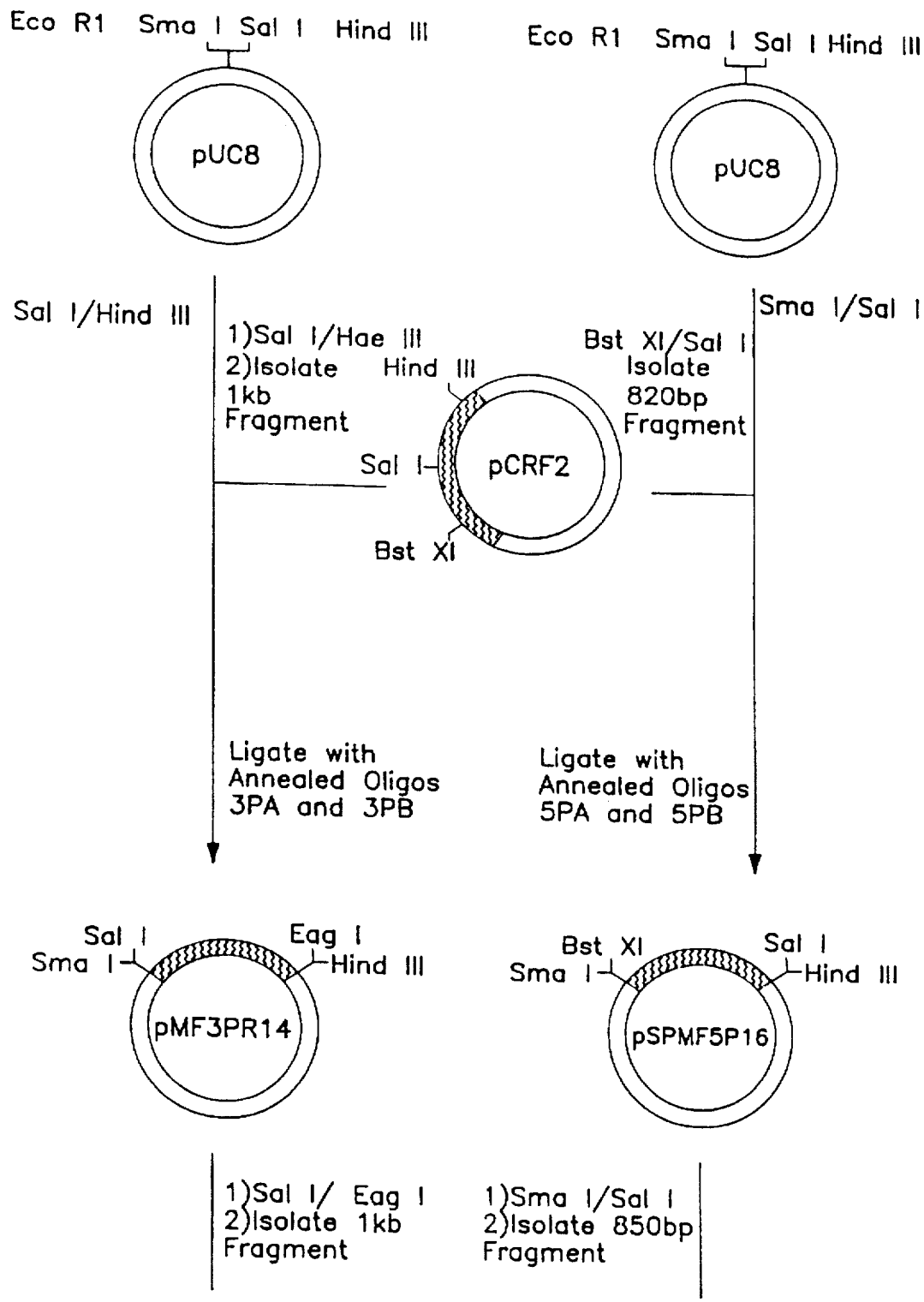
FIG. 2 schematically shows a method for the construction of plasmid pSPMFVC used to derive recombinant vaccinia virus vP455 expressing the NV fusion gene.
Figure 2B:
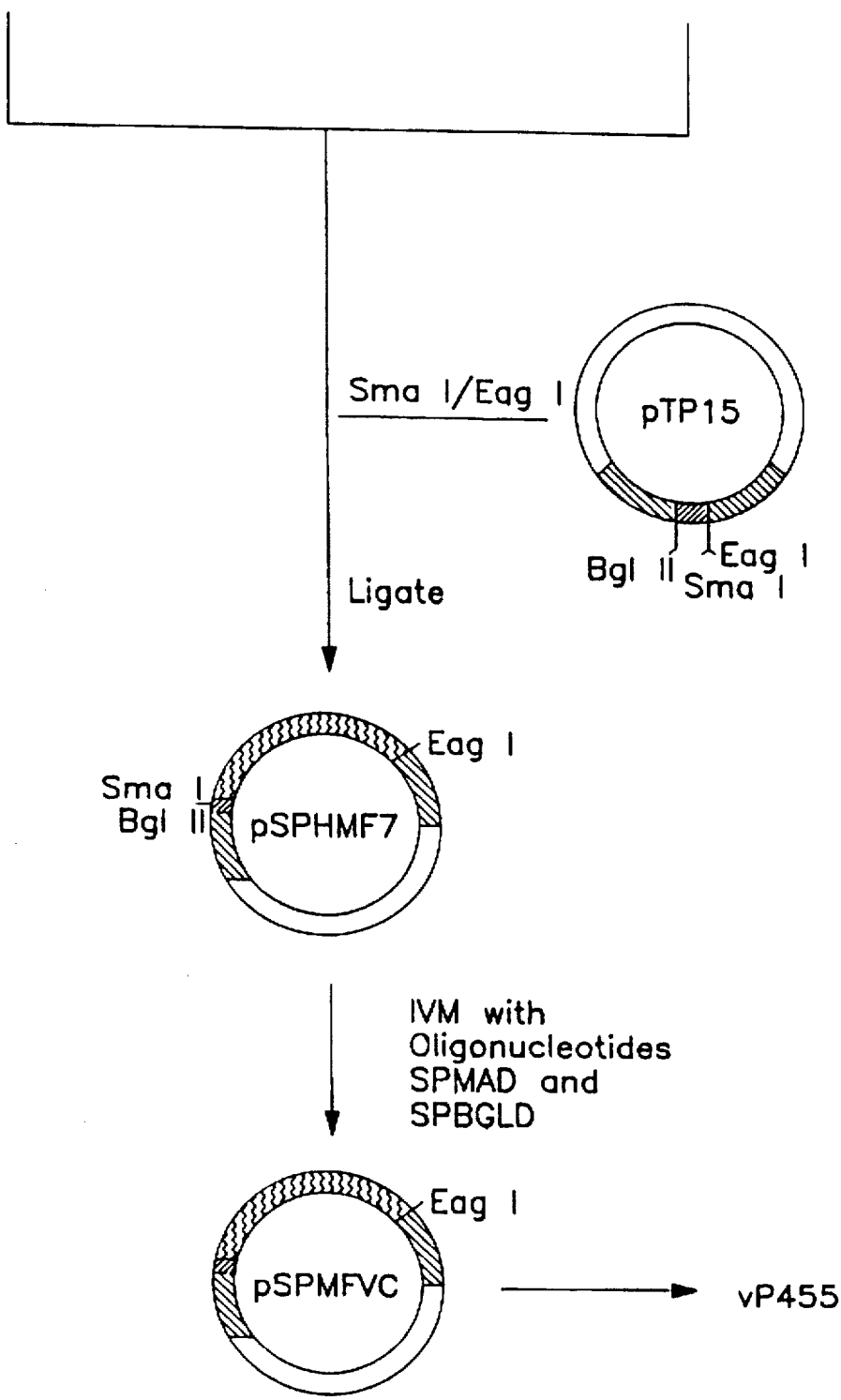

Referring now to FIG. 2, annealed oligonucleotides 3PA (SEQ ID NO:8) (5'-CCTAAAGCCTGATCTTACG-GGAACATCAAAATCCTATGTAAGGTCGCTCTGAT-TTTTATCGGCCGA-3') and 3PB (SEQ ID NO:9) (5'-AGCTTCGGCCGATAAAA-ATCAGAGCGACCTTACATAGGATTTTGATGTTCCC-GTAAGATCAGGCTTTAGG-3') containing the 3' end of the measles fusion gene, a vaccinia virus early transcription termination signal (Yuen et al., 1987) and EagI and HindIII ends were ligated to a 1 kbp SalI/HaeIII fragment from pCRF2 (obtained from C. Richardson, National Research Council of Canada (Biotechnology Institute), Montreal, Canada H3A 1A1) and pUC8 digested with SalI and HindIII. The resulting plasmid pMF3PR14 contains the 3' end of the 1 kbp fragment of the measles fusion gene.

Annealed oligonucleotides 5 PA (SEQ ID NO:10) (5'-GGGATGGGTCTCAAGGTGAACGTCTCTGCCATA-TTC-3') and 5 PB (SEQ ID NO:11) (5'-ATGGCAGAGACGTTCACCTTGAGACCCATCCC-3'), containing a 5' SmaI site and a 3' BstXI site, were ligated to a 820 bp BstXI/SalI fragment from pCRF2 and pUC8 digested with SmaI and SalI. The resultant plasmid pSPMF5P16 contains the 5' portion of the measles fusion gene. The 820 bp SmaI/SalI fragment from pSPMF5P16 and the 1 kbp SalI/EagI fragment from pMF3PR14 were ligated into pTP15 digested with SmaI and EagI. The plasmid pTP15 (Guo et al., 1989) contains the vaccinia virus early/late H6 promoter flanked by sequences from the HA locus of the vaccinia virus (Copenhagen strain) genome. The resultant plasmid containing the measles fusion gene juxtaposed 3' to the H6 promoter within the HA insertion plasmid was designated pSPHMF7.

Oligonucleotide directed mutagenesis was performed on pSPHMF7. Initially an in vitro mutagenesis reaction (Mandecki, 1982) was performed to create a precise ATG:ATG linkage of the H6 promoter with the measles fusion gene by removing the SmaI site using the oligonucleotide SPMAD (SEQ ID NO:12) (5'-TATCCGTTAAGTTTGTATGGTAATGGGTCTCAAG-GTGAACGTCT-3'). This resulted in the generation of pSPMF75M20. Subsequently, the BolII site at the 5' end of the H6 promoter was removed using oligonucleotide SPB-GLD (SEQ ID NO:13) (5'-AATAAATCACTTTTTTATACTA- ATTCTTTATTCTATACTTAAAAAGT-3') according to a known procedure (Mandecki, 1982). The resultant plasmid was designated pSPMFVC. This plasmid was used in in vitro recombination experiments with vaccinia virus vP410 as rescue virus to generate vP455.

EXAMPLE 3

Immunoprecipitation Analysis

In order to determine that recombinants vP455 and vP557 expressed authentic proteins, immunoprecipitation experiments were performed essentially as described (Taylor et al., 1990). Briefly, VERO cell monolayers were infected at 10 pfu per cell with either parental or recombinant viruses in the presence of $^{35}$S-methionine. The fusion protein was specifically precipitated from the infected cell lysate using a rabbit antiserum directed against a carboxy terminal fusion peptide. The hemagglutinin protein was specifically precipitated from the infected cell lysate using a polyclonal monospecific anti-hemagglutinin serum.

With respect to immunoprecipitation using a fusion specific serum, no radiolabelled products were detected in uninfected VERO cells, parentally infected VERO cells, or cells infected with the HA recombinant vP557. In cells infected with the fusion recombinant vP455, the fusion precursor $F_0$ with a molecular weight of approximately 60 kd and the two cleavage products $F_1$ and $F_2$ with molecular weights of 44 kd and 23 kd were detected. Similarly, with respect to immunoprecipitation of the glycosylated form of the HA protein with a molecular weight of approximately 75–77 kd, no products were detected in uninfected VERO cells, parental infected cells, or VERO cells infected with vP455.

In addition, immunofluorescence studies indicated that both proteins were expressed on the infected cell surface.

EXAMPLE 4

Cell Fusion Experiments

A characteristic of Morbillivirus cytopathogenicity is the formation of syncytia which arise by fusion of infected cells with surrounding uninfected cells followed by migration of the nuclei toward the center of the syncytium (Norrby et al., 1982). This has been shown to be an important method of viral spread, which for Paramyxoviruses can occur in the presence of hemagglutinin specific antibody (Merz et al., 1980). This ability has been assigned by analogy with other Paramyxoviruses to the amino terminus of the F1 peptide (Choppin et al., 1981; Novick et al., 1988; Paterson et al., 1987).

In order to determine that the measles proteins expressed in vaccinia virus were functionally active, VERO cell monolayers were inoculated with parental or recombinant viruses vP455 and vP557, respectively, at 1 pfu per cell. After 1 h absorption at 37° C. the inoculum was removed, the overlay medium replaced, and the dishes incubated overnight at 37° C. At 18 h post-infection, plates were examined with a microscope and photographed. No cell fusing activity was evident in VERO cells inoculated with parental virus, vP455 or vP557. However, when vP455 and vP557 were co-inoculated, efficient cell fusing activity was observed.

This result has recently been confirmed by Wild et al. (1991) who determined that syncytium formation in a variety of cell lines infected with measles/vaccinia virus recombinants required expression of both fusion and hemagglutinin genes. The result, however, is in contrast to a previous report (Alkhatib, 1990) which described cell fusion in 293 cells infected with high multiplicities of an adenovirus recombinant expressing the measles fusion protein. Similarly, it has been reported (Vialard et al., 1990) that cell fusion was observed in insect cells infected with a baculovirus recombinant expressing the measles fusion protein but only when incubated at pH 5.8. In neither case was the fusion activity enhanced by co-infection with the appropriate recombinant expressing the measles hemagglutinin protein. Variables which may be involved in the fusion process are cell type (Giraudon et al., 1984), pH of medium (Vialard et al., 1990) and level of expression of the fusion protein (Norrby et al., 1982).

EXAMPLE 5

Serological Test

The technique for virus neutralizing (VN) antibody testing was previously described in detail (Appel et al., 1973). Testing for CDV-VN antibody titers was made in VERO cells with the adapted Onderstepoort strain of CDV. Testing for MV-VN antibody titers was made in VERO cells with the adapted Edmonston strain of MV. The results of the serological tests are shown in Table 1.

Dogs immunized as described in Example 6 with either the vaccinia parental virus or vP455 expressing the measles fusion protein did not develop neutralizing antibody to MV. Dogs immunized with either vP557 expressing the HA protein or co-inoculated with both recombinants vP455 and vP557 did develop neutralizing antibodies after one inoculation. Levels of antibody were equivalent to those induced by inoculation with the attenuated Edmonston strain of MV.

TABLE 1

Measles virus neutralizing antibody titers in response to vaccination

| | | Days past vaccination | | | | | |
|---|---|---|---|---|---|---|---|
| Immunization | Dog No. | 0[a] | 7 | 14 | 21[b] | 28 | 35[c] |
| Vacc. | 4/1 | <1.0 | <1.0 | <1.0 | <1.0 | <1.0 | <1.0 |
| | 4/2 | <1.0 | <1.0 | <1.0 | <1.0 | <1.0 | <1.0 |
| vP455 | 4/3 | <1.0 | <1.0 | <1.0 | <1.0 | <1.0 | <1.0 |
| | 4/4 | <1.0 | <1.0 | <1.0 | <1.0 | <1.0 | <1.0 |
| vP557 | 4/5 | <1.0 | 2.2[d] | 2.9 | 2.9 | 3.4 | 3.4 |
| | 4/6 | <1.0 | 2.7 | 2.9 | 2.9 | 3.9 | 3.4 |
| vP455 & vP557 | 4/7 | <1.0 | 2.7 | 3.4 | 3.2 | 3.4 | 3.4 |
| | 4/8 | <1.0 | 2.5 | 2.9 | 2.9 | 3.6 | 2.9 |
| MV | 4/14 | | | | <1.0 | | 2.9 |
| | 4/15 | | | | <1.0 | | 3.2 | a)Time of first immunization
b)Time of second immunization (first immunization with MV)
c)Time of challenge
d)Titer expressed as $\log_{10}$ of last antibody dilution showing complete neutralization of infectivity in a microtiter neutralization test as described by Appel et al. (1973).

EXAMPLE 6

Animal Protection Studies

In order to determine whether expression of the measles virus proteins in dogs inoculated with the recombinants was sufficient to induce a protective immune response against CDV challenge, fourteen 10 week old specific pathogen free beagle dogs were studied. Blood samples were collected at the initiation of the experiment and repeatedly thereafter. Four groups with two dogs in each group were immunized with two injections three weeks apart. The first group received vaccinia virus only. The second group received vaccinia virus with an insert for the F protein of measles virus (vP455). The third group received vaccinia virus with an insert for the HA antigen of MV (vP557), and the fourth group received a combination of 2 and 3. Each dog was inoculated with approximately $4 \times 10^8$ pfu of vaccinia virus in 1 ml amounts (0.6 ml subcutaneously and 0.4 ml intramuscularly). Two control dogs received $10^5$ 50% tissue culture infectious doses (TCID$_{50}$) of the attenuated Edmonston strain of MV intramuscularly (1 ml amount) and two control dogs received $10^4$ TCID$_{50}$ of the attenuated Rockborn strain of CDV subcutaneously two weeks before challenge with virulent CDV. Two control dogs remained uninoculated before challenge.

All dogs were challenged by intranasal inoculation of 1 ml of tissue culture fluid containing $10^4$ TCID$_{50}$ of the Snyder Hill strain of virulent CDV two weeks after the last inoculation. The clinical reactions of the dogs were monitored by daily observations and recording of body temperature and by biweekly recording of weight gain or losses. Circulating blood lymphocytes were counted before challenge and on days post challenge (dpc) 3, 5, 7 and 10. Virus isolation from buffy coat cells by co-cultivation with dog lung macrophages (Appel et al., 1967) was attempted on dpc 3, 5, 7 and 10. Blood samples for serological tests were collected before vaccination and in weekly intervals until time of challenge, and on dpc 7, 10 and 20.

The results of challenge are shown in Table 2

EXAMPLE 7

Additional Vaccinia/Measles Contructs

Figure 3:
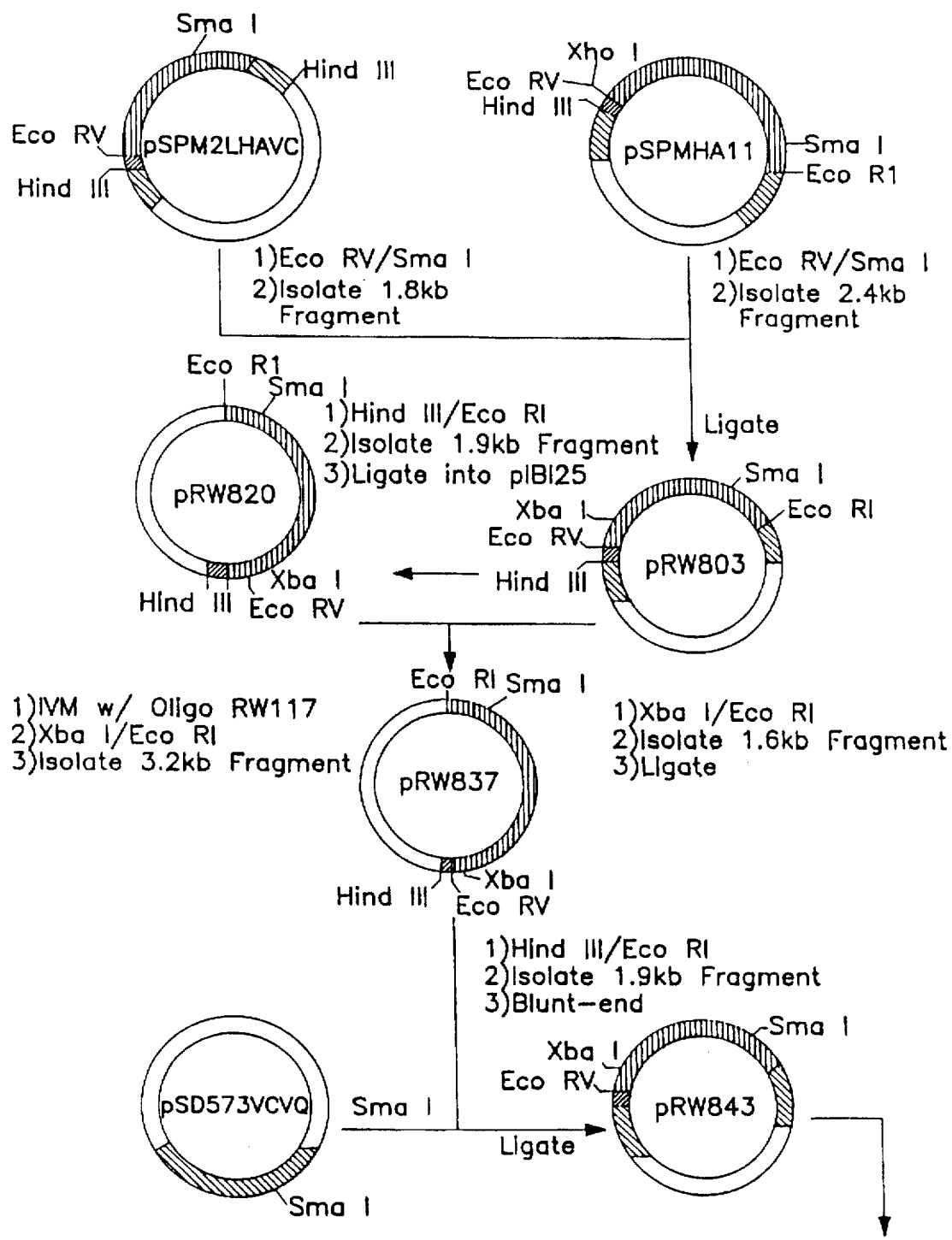
FIG. 3 schematically shows a method for the construction of plasmid pRW843 used to derive recombinant vaccinia virus vP756 expressing the NV hemagglutinin gene.

Referring now to FIG. 3, a second vaccinia virus recombinant containing the measles HA gene within the tk locus was generated (vP756) using insertion plasmid pRW843. pRW843 was constructed in the following manner. A 1.8 kbp EcoRV/SmaI fragment containing the 3'-most 24 bp of the H6 promoter fused in a precise ATG:ATG configuration with the HA gene lacking the 3'-most 26 bp was isolated from pSPM2LHAVC. This fragment was used to replace the 1.8 kbp EcoRV/SmaI fragment of pSPMHA11 to generate pRW803. Plasmid pRW803 contains the entire H6 promoter linked precisely to the entire measles HA gene.

In the confirmation of previous constructs with the measles HA gene it was noted that the sequence for codon 18 (CCC) was deleted as compared to the published sequence (Alkhatib et al., 1986). The CCC sequence was replaced by oligonucleotide mutagenesis via the Kunkel method (Kunkel, 1985) using oligonucleotide RW117 (SEQ ID NO:14) (5'-GACTATCCTACTTCCCTT GGGATGGGGGTTATCTTTGTA-3').

Pro 18

Single stranded template was derived from plasmid pRW819 which contains the H6/HA cassette from pRW803 in pIBI25 (IBI, New Haven, Conn.). The mutagenized plasmid containing the inserted (CCC) to encode for a proline residue at

TABLE 2

Effects of immunization on clinical signs after exposure of dogs to virulent CDV

| | | | | No. of days after inoculation with virulent CDV | | | |
|---|---|---|---|---|---|---|---|
| Immunization | Dog Number | Depression | Weight Loss | Elevated Body Temp.[a] | Lympho-penia[b] | Virus Isolation[c] | Death |
| Vacc. | 4/1 | 4–10[d] | 3–10 | 4, 5, 7, 10 | 7–10 | 3–7 | 10 |
| | 4/2 | 4–10[d] | 3–10 | 4, 5, 8–10 | 3–10 | 3–7 | 10 |
| vP455 | 4/3 | 4–8 | 7–10 | 4, 5, 7–10 | 5, 7 | 5–7 | — |
| | 4/4 | 4–6 | 7–10 | 4–6 | 7 | 5–7 | — |
| vP557 | 4/5 | ND[e] | ND | 6, 7 | 10 | 7 | — |
| | 4/6 | ND | ND | ND | ND | ND | — |
| vP455 & vP557 | 4/7 | ND | ND | 7 | 7 | 7 | — |
| | 4/8 | ND | 7 | 6 | ND | 7 | — |
| MV | 4/14 | ND | ND | ND | 7 | ND | — |
| | 4/15 | ND | 7 | 5 | 5 | ND | — |
| CDV-Ro | 4/16 | ND | ND | ND | ND | ND | — |
| | 4/17 | ND | ND | ND | ND | ND | — |
| None | 4/18 | 6, 14–17[d] | 7–17 | 5, 7 | 13–17 | 10 | 17 |
| | 4/19 | 4–10[d] | 3–10 | 4, 5, 7 | 3, 7, 10 | 3–10 | 10 |

[a]Above 39.5° C.
[b]Less than $2 \times 10^3$ Lymphocytes per mm$^3$
[c]Isolated from buffy coat cells co-cultivated with dog lung macrophages
[d]Dog became dehydrated and was euthanized
[e]None detected Non-immunized control dogs and dogs vaccinated with parental vaccinia virus developed clinical signs of severe disease and were euthanized when dehydration was evident. Both dogs immunized with vP455 showed some signs; of infection with CDV including weight loss, elevated body temperature, and lymphopenia although these symptoms were of shorter duration than were seen in control dogs. Nonetheless, both dogs survived lethal challenge with CDV. Dogs inoculated with vP557 or co-inoculated with both recombinants showed minimal signs of infection and survived challenge. Dogs inoculated with either attenuated Edmonston strain of MV or the attenuated Rockborn strain of CDV also survived challenge with minimal signs of disease.

codon 18 was designated pRWB820. The sequence between the HindIII and XbaI sites of pRW820 was confirmed by nucleotide sequence analysis. The HindIII site is situated at the 5' border of the H6 promoter while the XbaI site is located 230 bp downstream from the initiation codon of the HA gene. A 1.6 kbp XbaI/EcoRI fragment from pRW803, containing the HA coding sequences downstream from the XbaI and including the termination codon, was used to replace the equivalent fragment of pRW820 resulting in the generation of pRW837. The mutagenized expression cassette contained within pRW837 was derived by digestion with HindIII and EcoRI, blunt-ended using the Klenow fragment of E. coli DNA polymerase in the presence of 2 mM dNTPs, and inserted into the SmaI site of pSD573VCVQ to yield pRW843. The plasmid pRWS43 was used in in vitro recombination experiments with vP618 as the rescue virus to yield vP756. Parental virus vP618 is a Copenhagen strain virus from which the thymidine kinase, hemorrhagic and A-type inclusion genes have been deleted. Recombinant vP756 has been shown by immunoprecipitation analysis to correctly express a hemagglutinin glycoprotein of approximately 75 kd.

Figure 4:
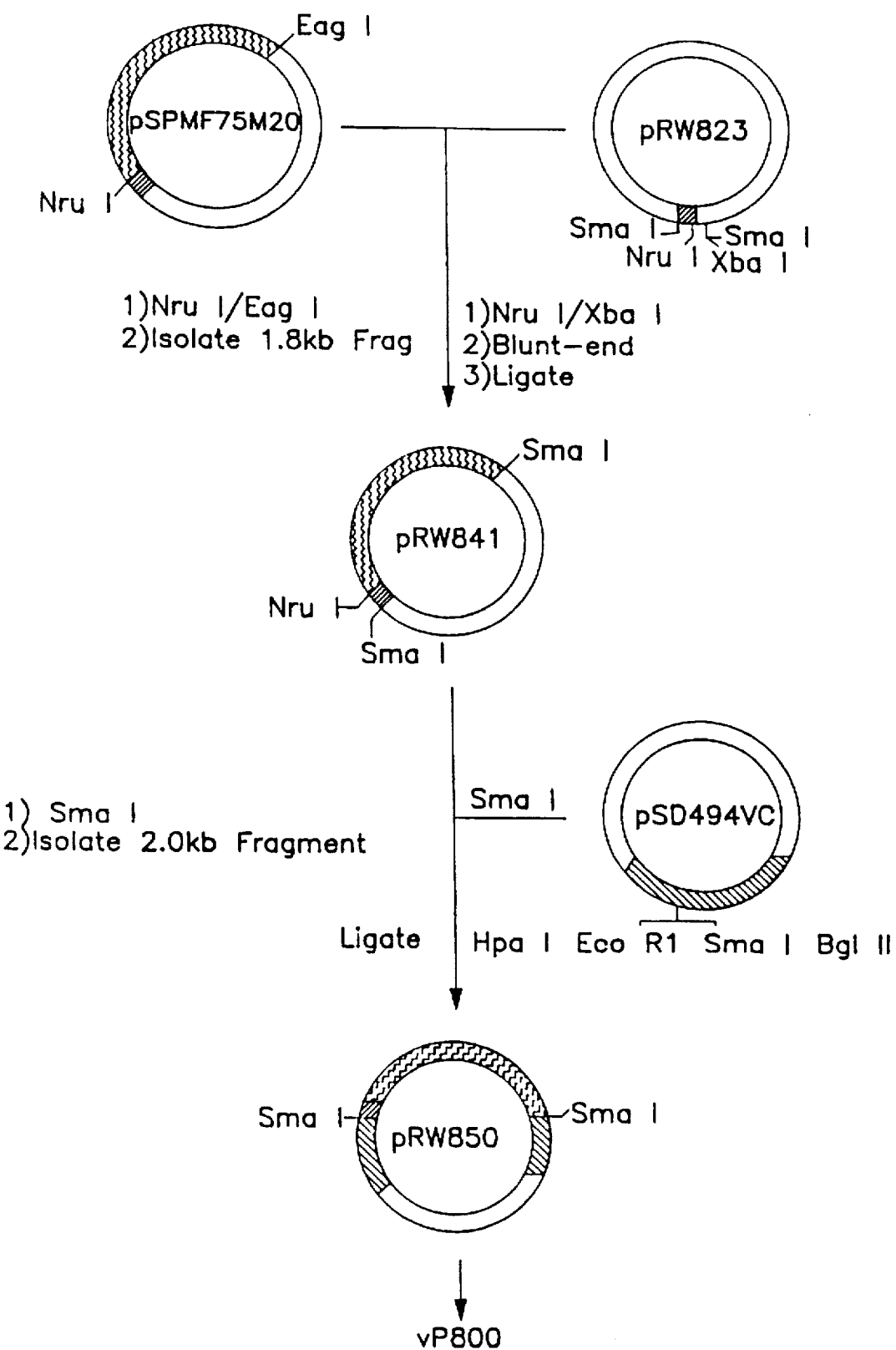
FIG. 4 schematically shows a method for the construction of plasmid pRW850 used to derive recombinant vaccinia virus vP800 expressing the MV fusion gene.

Referring now to FIG. 4, a second vaccinia virus recombinant (vP800) harboring the measles fusion gene in the ATI locus of the genome was generated using insertion plasmid pRW850. To construct pRW850, the following manipulations were performed. The plasmid pSPMF75M20 containing the measles fusion gene linked in a precise ATG:ATG configuration with the H6 promoter was digested with NruI and EagI. The 1.7 kbp blunt ended fragment containing the 3'-most 28 bp of the H6 promoter and the entire fusion gene was isolated and inserted into pRW823 digested with NruI and XbaI and blunt-ended. The resultant plasmid pRW841 contains the H6 promoter linked to the measles fusion gene in the pIBI25 plasmid vector (IBI, New Haven, Conn.). The H6/measles fusion expression cassette was derived from pRW841 by digestion with SmaI and the resulting 1.8kbp fragment was inserted into pSD494VC digested with SmaI to yield pRW850. The plasmid pRW850 was used in in vitro recombination experiments with vP618 as the rescue virus to yield vP800. Recombinant vP800 has been shown by immunoprecipitation analysis to express an authentically processed fusion glycoprotein.

EXAMPLE 8

Assessment of Measles Neutralizing Antibody in Guinea Pigs and Rabbits Inoculated with vP455

Two rabbits were inoculated intradermally at 5 sites with a total of $1 \times 10^8$ pfu of recombinant vP455 expressing the measles fusion protein. Both rabbits were boosted with an identical inoculation at week 12. Serial bleeds were collected, and at week 14, two weeks after the boost, the rabbits were tested for the presence of serum neutralizing antibodies.

Four guinea pigs were inoculated subcutaneously with $1 \times 10^8$ pfu each of recombinant vP455. An identical booster inoculation was given at 21 days. Serial bleeds were collected.

The presence of measles virus serum neutralizing antibody was assessed using a microtiter test (Appel et al., 1973) using 10 TCID$_{50}$ of virus per microtiter well. The results are shown in Table 3. E HRI:2370.APP 30

TABLE 3

Results of measles virus serum neutralizing antibodies in guinea pigs and rabbits inoculated with vP455

| | Week Post-Inoculation | | | | | | |
|---|---|---|---|---|---|---|---|
| | 0 | 2 | 3 | 4 | 5 | 7 | 14 |
| Animal Guinea Pig | | | | | | | |
| 1 | N.D.[a] | N.D. | N.D.–.8[b] | 1.3–1.3 | 1.3–1.5 | 1.3 | N.T.[c] |
| 2 | N.D. | N.D. | .8–1.0 | .8–1.3 | 1.3–1.5 | N.D. | N.T. |
| 3 | N.D. | N.D. | N.D.–.8 | .8–1.5 | 1.0–1.3 | 1.0 | N.T. |
| 6 | N.D. | N.D. | .8–.8 | .8–.8 | 1.0–1.3 | 1.0 | N.T. |

TABLE 3-continued

Results of measles virus serum neutralizing antibodies in guinea pigs and rabbits inoculated with vP455

| | Week Post-Inoculation | | | | | | |
|---|---|---|---|---|---|---|---|
| | 0 | 2 | 3 | 4 | 5 | 7 | 14 |
| Rabbit | | | | | | | |
| W44 | N.D. | N.T. | N.T. | N.T. | N.T. | N.T. | 1.5 |
| W86 | N.D. | N.T. | N.T. | N.T. | N.T. | N.T. | 1.5 |

[a] Not detectable
[b] Results of two assays
[c] Not tested

EXAMPLE 9

Generation of Measles Virus Recombinant Canrypox Virus

Measles/canarypox virus recombinants were developed using a similar strategy to that previously described for fowlpox virus (Taylor et al., 1988a,b).

Plasmids for insertion of the measles F and HA genes into canarypox virus were generated as follows.

Figure 5:
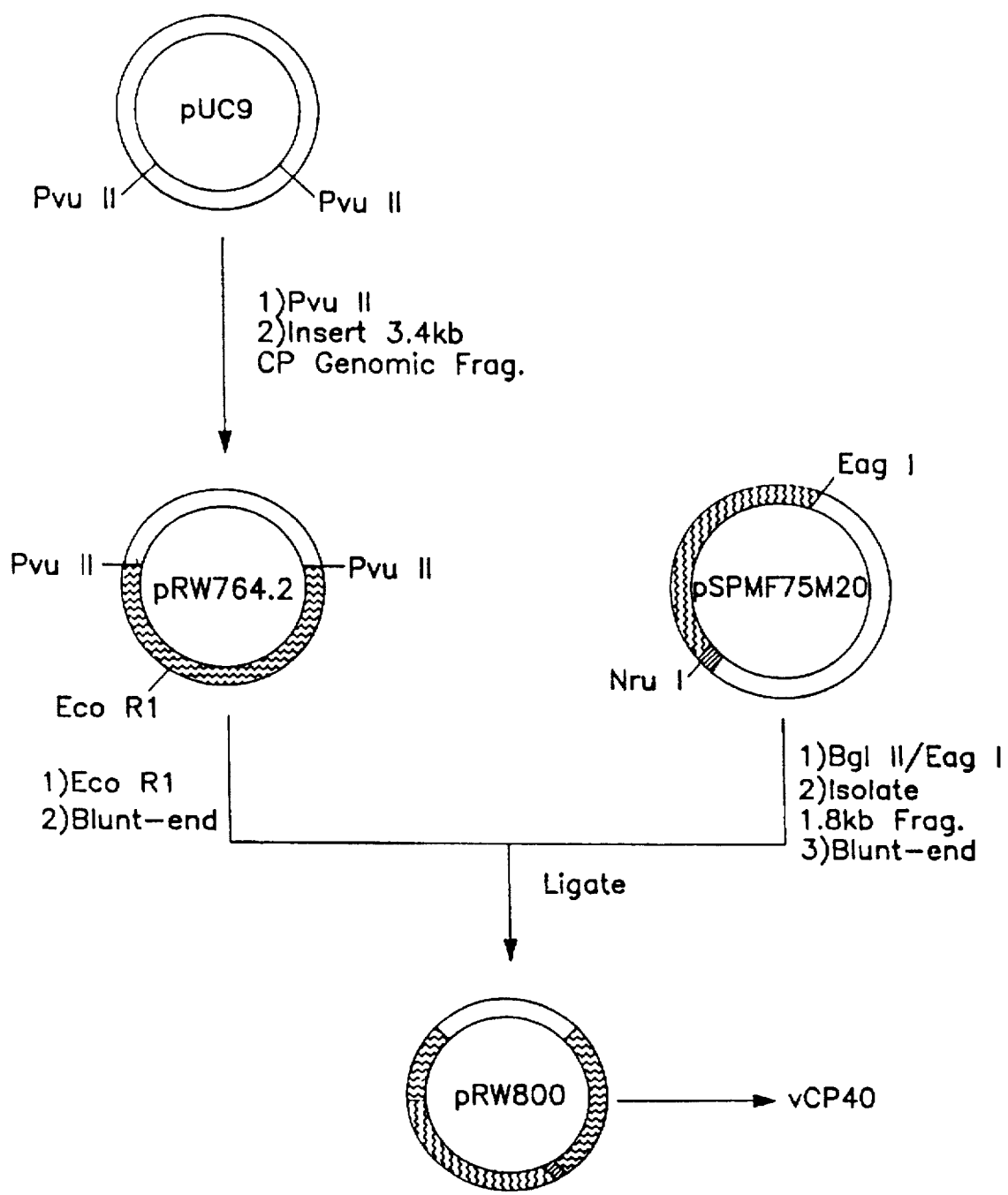
FIG. 5 schematically shows a method for the construction of plasmid pRW800 used to derive recombinant canarypox virus vCP40 expressing the MV fusion gene.

Referring now to FIG. 5, the 1.8 kbp blunt-ended BglII/EagI fragment from pSPMF75M20 containing the H6 promoted measles F gene was inserted into the blunt-ended EcoRI site of pRW764.2. Plasmid pRW764.2 contains a 3.4 kbp PvuII fragment from the canarypox genome having a unique EcoRI site which has been determined to be non-essential for viral replication. The resultant plasmid containing the measles F gene was designated pRW800 and was used in recombination experiments with canarypox as the rescuing virus to generate vCP40.

Figure 6:
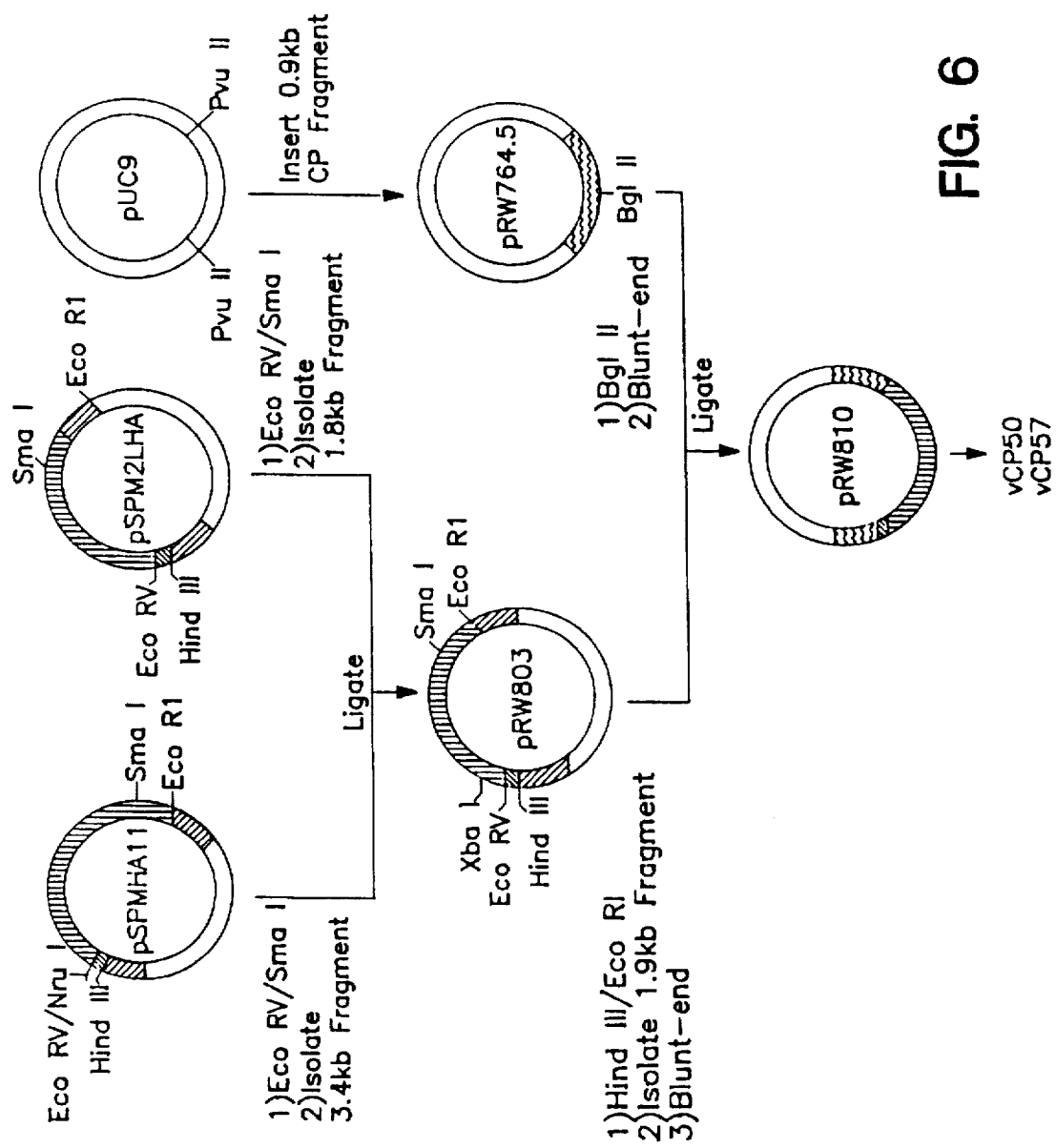
FIG. 6 schematically shows a method for the construction of plasmid pRW810 used to derive recombinant canarypox viruses vCP50 expressing the MV hemagglutinin gene and vCP57 co-expressing the MV fusion and hemagglutinin genes.

Referring now to FIG. 6, the 1.8 kbp EcoRV/SmaI fragment from pSPM2LHA containing the 3'-most 28 bp of the H6 promoter fused in a precise ATG:ATG configuration with HA was inserted between the EcoRV and SmaI sites of pSPMHA11 The resultant plasmid was designated pRW803. A 2 kbp HindIII/EcoRI fragment of pRW803 containing the H6 promoted measles HA gene was blunt-ended and inserted into the blunt-ended BglII site of plasmid pRW764.5. Plasmid pRW764.5 contains an 800bp PvuII fragment of the canarypox genome having a unique BglII site which has previously been determined to be non-essential for viral growth. This insertion created plasmid pRW810 which was used in recombination tests to generate vCP50.

Insertion of the measles F and HA sequences individually led to the development of recombinants vCP40 and vCP50, respectively. In order to create a double recombinant, the single F recombinant vCP40 was used as a rescue virus for insertion of the HA gene contained in pRW810. This led to the development of double recombinant vCP57.

EXAMPLE 10

Immunoprecipitation Analysis

In order to confirm that recombinants vCP40, vCP50 and vCP57 expressed authentic proteins, immunoprecipitation analysis was performed using mono-specific sera directed against either the HA or F proteins. A correctly processed fusion polypeptide was specifically precipitated from lysates of cells infected with vCP40 and vCP57. The fusion precursor $F_0$ with a molecular weight of approximately 60 kd and the two cleavage products $F_1$ and $F_2$ with molecular weights of approximately 44 and 23 kd, respectively, were detected. No fusion specific products were detectable in uninfected CEF cells, parentally infected CEF cells or CEF cells infected with the HA recombinant vCP50. Similarly, a glycoprotein of approximately 75 kd was specifically precipitated from CEF cells infected with the single HA recombinant vCP50 and double recombinant vCP57. No HA specific products were detected in uninfected cells, parentally infected cells or cells infected with fusion recombinant vCP40.

EXAMPLE 11

Cell Fusion Experiments

In order to determine that the measles virus recombinants were functionally active, cell fusion assays were performed. VERO cell monolayers were infected with 1 pfu per cell of CP parental or recombinant viruses and examined for cytopathic effects at 18 hours post infection. No cell fusing activity was evident in VERO cells inoculated with parental, vCP40 or vCP50 viruses. However, when VERO cells were inoculated with the double recombinant vCP57 or when cells are co-infected with both vCP40 and vCP50, efficient cell fusing activity is evident.

EXAMPLE 12

Serological Tests

Dogs inoculated as described in Example 13 with the canarypox/HA recombinant vCP50, vaccinia/HA recombinant vP557, the canarypox/HA/F double recombinant vCP57 or co-inoculated with vP455 and vP557 developed significant serum neutralizing antibody to measles virus after one inoculation. Neither of the two dogs inoculated with the canarypox/F recombinant vCP40 developed neutralizing antibody after one or two inoculations. The results of the serological tests are shown in Table 4.

In addition, guinea pigs inoculated with the VCP40 recombinant did develop low but reproducible levels of serum neutralizing antibody.

TABLE 4

Measles virus neutralizing antibody titers (in $\log^{10}$)

| Immunization | Dog No. | 0[a] | 7 | 14 | 21[b] | 28 | 35[c] |
|---|---|---|---|---|---|---|---|
| Canary pox virus | 9/1 | <1.0 | <1.0 | <1.0 | <1.0 | <1.0 | <1.0 |
| (CPV) | 9/2 | <1.0 | <1.0 | <1.0 | <1.0 | <1.0 | <1.0 |
| vCP50 | 9/3 | <1.0 | 2.7[d] | 2.9 | 3.2 | 4.4 | 4.1 |
|  | 9/4 | <1.0 | 1.7 | 2.7 | 2.7 | 3.9 | 3.9 |
| vCP40 | 9/5 | <1.0 | <1.0 | <1.0 | <1.0 | <1.0 | <1.0 |
|  | 9/6 | <1.0 | <1.0 | <1.0 | <1.0 | <1.0 | <1.0 |
| vCP57 | 9/7 | <1.0 | 2.0 | 2.7 | 2.5 | 3.9 | 3.6 |
|  | 9/8 | <1.0 | 1.0 | 2.2 | 2.0 | 3.6 | 3.4 |
| vP455 | 9/9 | <1.0 | <1.0 | <1.0 | 1.0 | 1.0 | 1.0 |
| vP557 | 9/10 | <1.0 | 2.9 | 2.5 | 3.2 | 3.4 | 3.4 |
| vP455 & vP557 | 9/11 | <1.0 | 1.3 | 2.9 | 2.9 | 2.9 | 2.9 |
| MV | 9/12 |  |  |  | <1.0 | 2.5 | 2.5 |
| Control | 9/13 |  |  |  |  |  | <1.0 |
|  | 9/14 |  |  |  |  |  | <1.0 |
| CDV-Ro | 9/15 |  |  |  | <1.0 | <1.0 | <1.0 |

[a]Time of first immunization.
[b]Time of second immunization. (First immunization with MV and CDV-Ro).
[c]Time of challenge.
[d]Assessment of serum neutralization titers assessed in known manner (Appel et al., 1973).

EXAMPLE 13

Animal Protection Studies

In order to determine whether non-replicating canarypox vectors expressing measles virus proteins would induce a protective immune response against CDV challenge, ten week old specific pathogen free beagle dogs were inoculated with canarypox parental and recombinant viruses. Two dogs were inoculated simultaneously with two subcutaneous injections of $1\times10^8$ pfu of each recombinant at three week intervals. For comparison, one dog was inoculated in the same regimen with each of the single vaccinia virus recombinants vP455 and vP557 and a combination of both. One dog was also inoculated intramuscularly with one dose of $10^5$ TCID$_{50}$ of the attenuated Edmonston strain of MV. One dog was inoculated subcutaneously with one dose of $10^4$ TCID$_{50}$ of the attenuated Rockborn strain of CDV. Dogs were challenged two weeks after the final inoculation via intranasal inoculation with a lethal dose of $10^4$ TCID$_{50}$ of the virulent Snyder Hill strain of CDV. Clinical reactions of dogs were monitored daily. The results are shown in Table 5.

TABLE 5

Effects of immunization on clinical signs after exposure of dogs to virulent CDV

| | | No. of days after inoculation with virulent CDV | | | | |
|---|---|---|---|---|---|---|
| Immunization | Dog No. | Depression | Elevated Wt. Loss | Lympho Body Temp.[a] | Virus penia[b] | Isolation[c] |
| Canary pox | 9/1 | 4–10[d] | 3–10 | 4, 5, 7, 8 | 5–10 | 3–10 |
| virus (CPV) | 9/2 | 4–10[d] | 7–10 | 4, 5, 7, 8 | 3–10 | 3–10 |
| vCP50 | 9/3 | ND[e] | 7–10 | 5–7 | 5–7 | 7 |
|  | 9/4 | ND | 7 | 6, 7 | 7 | ND |
| vCP40 | 9/5 | 4–10 | 3–10 | 4 | 5–10 | 5–7 |
|  | 9/6 | 4–6 | 3–10 | 4–6 | 5 | 5–7 |
| vCP57 | 9/7 | ND | 7–10 | 5, 6 | 5 | ND |

TABLE 5-continued

Effects of immunization on clinical signs after exposure of dogs to virulent CDV

| | | | | No. of days after inoculation with virulent CDV | | | |
|---|---|---|---|---|---|---|---|
| Immunization | Dog No. | Depression | Elevated Wt. Loss | Lympho Body Temp.[a] | Virus penia[b] | Isolation[c] | |
| | 9/8 | ND | 7–10 | 4–7, 10 | 7–10 | 5–7 | |
| vP455 | 9/9 | 6–8 | 7–10 | 4, 5, 8, 9 | 5–10 | 3–10 | |
| vP557 | 9/10 | ND | 3–10 | ND | ND | ND | |
| vP455 & vP557 | 9/11 | ND | 3–10 | ND | 5–7 | ND | |
| MV | 9/12 | ND | 7–10 | ND | 5 | 5 | |
| None | 9/13 | 4–10[d] | 3–10 | 4–6 | 5–10 | 5–10 | |
| | 9/14 | 4–10[d] | 3–10 | 4–5 | 3–10 | 5–7 | |
| CDV-Ro | 9/15 | ND | ND | ND | ND | ND | |

[a]Above 39.5° C.
[b]Less than 2 × 10³ Lymphocytes per mm³.
[c]Isolated from buffy coat cells co-cultivated with dog lung macrophages in known manner (Appel et al., 1967).
[d]Dog became dehydrated and was euthanized.
[e]None detected.

No adverse reactions to vaccination were noticed in any of the dogs during the course of the experiment. The two dogs immunized with parental canarypox virus and two non-immunized control dogs showed severe disease after challenge with virulent CDV. All four dogs became depressed, showed elevated body temperature, weight loss, lymphopenia and severe dehydration. Dogs immunized with CDV-Rockborn developed serum neutralizing antibodies against CDV but not against MV prior to challenge and survived challenge, symptom free. Dogs immunized with attenuated MV developed serum neutralizing antibodies to MV but not CDV prior to challenge, and survived challenge with mild signs of infection. Dogs inoculated with vCP50, vCP57, vP557 or co-inoculated with vP455 and vP557 developed significant serum neutralizing antibody to MV after one inoculation and survived challenge with only minor signs of infection.

EXAMPLE 14

Additional Canarypox/Measles Constructs

Figure 7:
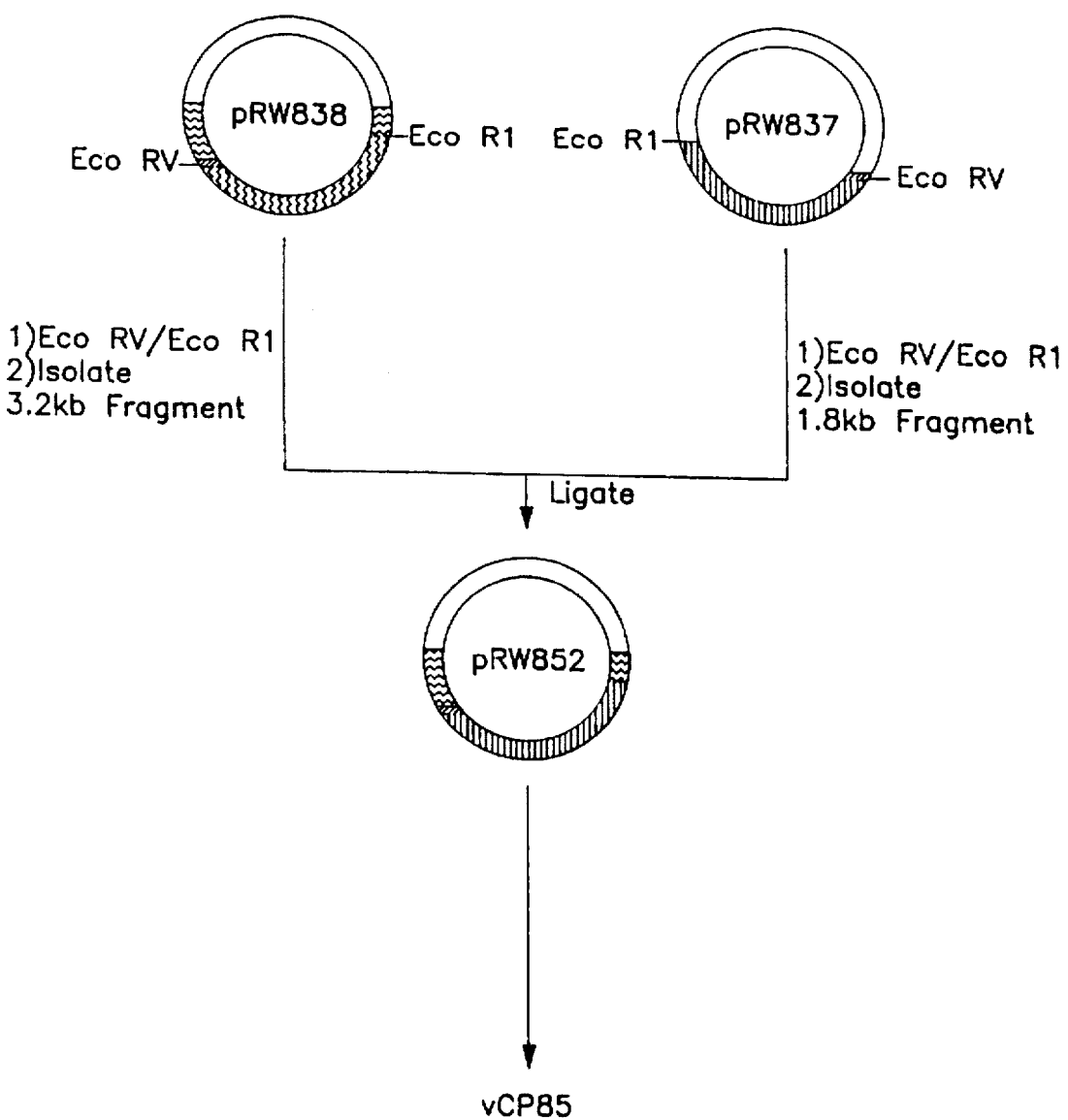
FIG. 7 schematically shows a method for the construction of plasmid pRW852 used to derive recombinant canarypox virus vCP85 expressing the MV hemagglutinin gene.
Figure 8:
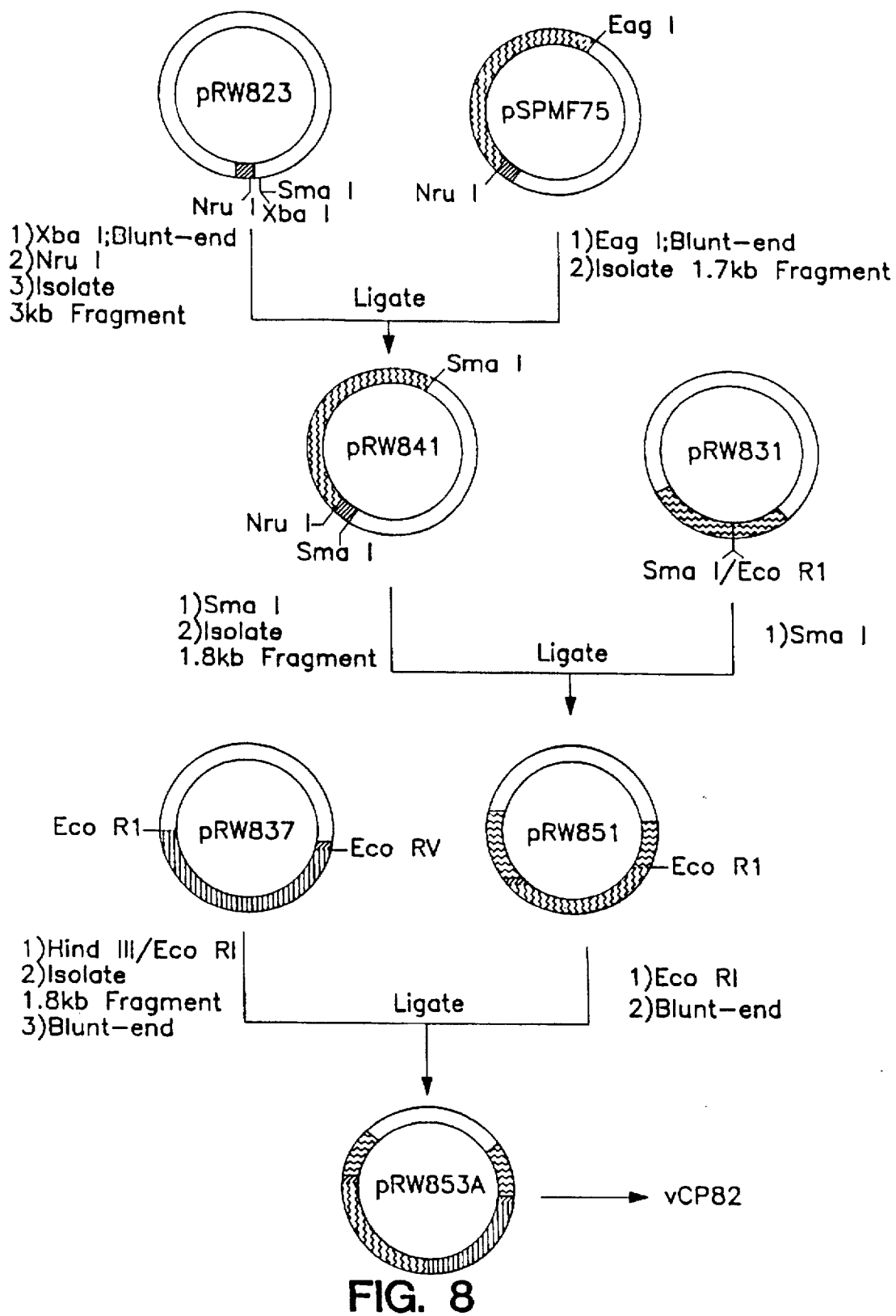
FIG. 8 schematically shows a method for the construction of plasmid pRW853A used to derive recombinant canarypox virus vCP82 co-expressing the MV hemagglutinin and fusion genes.

Referring now to FIG. 7, to generate a canarypox virus recombinant expressing the MV HA gene the following insertion plasmids were created. A 1.8 kbp EcoRV/EcoRI fragment from pRW837 containing the 3'-most 26 bp of the H6 promoter linked precisely to the measles HA, was ligated to a 3.2 kbp EcoRV/EcoRI fragment from pRW838. The pRW838 derived fragment includes the 5' portion of the H6 promoter and C5 locus flanking arms. Plasmids pRW838 and pRW831 (see below) were derived as follows.

An 880 bp PvuII canarypox genomic fragment was inserted between the PvuII sites of pUC9. the resultant plasmid was designated pRW764.5. The nucleotide sequence of the 880 bp canarypox fragment was determined using the modified T7 enzyme Sequenase™ Kit (United States Biochemical, Cleveland, Ohio) according to manufacturer's specifications. Sequence reactions utilized custom synthesized primers (17–18 mers) prepared with the Biosearch 8700 (San Rafael, Calif.) or Applied Biosystems 3800 (Foster City, Calif.). This enabled the definition of the C5 open reading frame.

To specifically delete the C5 open reading frame, pRW764.5 was partially cut with RsaI and the linear product was isolated. The RsaI linear fragment was recut with BglII and the pRW764. 5 fragment with a RsaI-BglII deletion from position 156 to position 462 was isolated and used as a vector for the following synthetic oligonucleotides: RW145 (SEQ ID NO:15): (5'-ACTCTCAAAAGCTTCCCG-GGAATTCTAGCTAGCTAGTTTTTATAAA-3') RW146 (SEQ ID NO:16): (5'-GATCTTTATAAAAACTAG-CTAGCTAGAATTCCCGGGAAGCTTTTGAGAGT-3') Oligonucleotides RW145 and RW146 were annealed and inserted into the pRW764.5 RsaI-BglII vector described above. The resulting plasmid is pRW831.

This C5 deletion plasmid was constructed without interruption of other canarypox virus open reading frames. The C5 coding sequence was replaced with the above annealed oligonucleotides (RW145 and RW146) which include the restriction sites for HindIII, SmaI, and EcoRI.

The plasmid pRW838, was derived from pRW831 by the insertion of a SmaI fragment containing the Rabies G gene (Taylor et al., 1988b) juxtaposed 3' to the vaccinia virus H6 promoter. Ligation of the 1.8 kbp EcoRV/EcoRI fragment from pRW837 with the 3.2 kbp EcoRV/EcoRI fragment from pRW838 led to the construction of plasmid pRW852. Plasmid pRW852 was used in recombination experiments with a canarypox isolate designated ALVAC to yield vCP85. ALVAC is a plaque cloned isolate of canarypox virus (CPV) derived from the Rentschler strain, a highly attenuated strain of CPV used for vaccination of canaries. ALVAC was deposited under the terms of the Budpest Treaty on Nov. 14, 1996 with the American Type Culture Collection (ATCC), 12301 Parklawn Drive, Rockville, Md. 20852, USA, ATCC accession number VR-2547. Replication of ALVAC and derived recombinants is restricted to avian species. Immunoprecipitation analysis has confirmed that a protein of approximately 75 kd recognized by a rabbit anti-HA serum is expressed in CEF cells infected with recombinant vCP85.

Referring now to FIG. 8, to generate a canarypox virus recombinant harboring both the MV HA and F genes the following constructs were engineered. SmaI restriction sites were added to the ends of the H6 promoted measles fusion gene. To accomplish this, pRW823, which is pIBI25 containing the vaccinia virus H6 promoter, was digested downstream of the promoter sequence at the XbaI site. The ends were blunted with the Klenow fragment of the *E. coli* DNA polymerase in the presence of 2mM dNTPs. The blunt-ended DNA was subsequently digested with NruI to liberate a 3.0 kbp fragment containing the 5'-most 100 bp of the H6 promoter. This fragment was isolated and ligated to a 1.7 kbp blunt-ended EagI/NruI fragment from pSPMF75. The resultant plasmid was designated as pRW841.

The 1.8 kbp SmaI fragment derived by digestion of pRW841 was inserted into the C5 deletion vector, pRW831. The plasmid pRW851 was linearized at the EcoRI site situated 3' to the fusion gene and was blunt-ended with the Klenow fragment of the *E. coli* DNA polymerase in the presence of 2 mM dNTPs. The plasmid pRW837, containing the measles HA gene juxtaposed 3' to the H6 promoter sequences, was digested with HindIII and EcoRI and blunt-ended with the Klenow fragment. The resultant 1.8 kbp fragment was isolated and inserted into pRW851 that had been linearized with EcoRI and blunt-ended. The resultant plasmiid, which contains both genes in a tail to tail configuration, was designated pRW853A and was utilized in in vitro recombination experiments with canarypox (ALVAC) as the rescue virus to generate vCP82 also designated ALVAC-MV. Expression analysis using immunoprecipitation and immunofluorescence confirmed that in cells infected with recombinant vCP82 authentically processed HA and F proteins were expressed. The recombinant was also functional for cell fusing activity.

Results of Serological Analysis of Sera of Rabbits and Guinea Pigs Inoculated with ALVAC-MV (vCP82)

Four guinea pigs were inoculated by the subcutaneous route with ALVAC-MV (vCP82). Two animals (026 and 027) each received $1\times10^8$ pfu and two animals (028 and 029) each received $1\times10^7$ pfu. At 28 days, animals were re-inoculated with an identical dose. Two rabbits were inoculated with $1\times10^8$ pfu of ALVAC-MV (vCP82) by the subcutaneous route. At 28 days, animals were re-inoculated with an identical dose. Serial bleeds of these animals were analyzed for measles virus neutralizing activity using either a microtiter neutralization test described by Appel and Robson (1973) or a plaque reduction neutralization test described by Albrecht et al. (1981). In addition, sera were analyzed for the presence of antibody capable of blocking measles virus induced cell-cell fusion in an anti-fusion assay performed as described in Merz et al. (1980).

The results of analysis for the presence of measles virus serum neutralizing antibody are shown in Tables 6 and 7. Both guinea pigs (026 and 027) receiving $1\times10^8$ pfu of ALVAC-MV sero-converted after a single inoculation and sera showed an antibody rise after the booster inoculation. One animal (029) receiving $1\times10^7$ pfu also sero-converted after one inoculation. The fourth animal (028) did not show a detectable response after one inoculation but did achieve equivalent titers after the second inoculation.

Rabbit sera were also analyzed using a plaque reduction neutralization method. The results are shown in Table 7. Both animals sero-converted after one inoculation. Sera of rabbit 063 was tested by both the micro-titer neutralization test and the plaque reduction neutralization test. Titers achieved were similar using both methods. It has been reported that a minimal serum neutralizing titer of 1.2 to 1.9 in vaccinated children is required for protection from disease (Lennon and Black, 1986; Black et al., 1984). Using this criteria, all animals, except the one guinea-pig which did not sero-convert until the second inoculation showed a protective level of antibody after one inoculation.

TABLE 6

Serological analysis of sera of guinea pigs inoculated with ALVAC-MV (vCP82): Analysis performed by microtiter serum neutralization assay.

| | Days post-inoculation | | | | | | |
|---|---|---|---|---|---|---|---|
| Animal | 0 | 14 | 21 | 28[c] | 42 | 48 | 56 |
| Guinea pigs | | | | | | | |
| 026[d] | — | N.T.[a] | 1.25[b] | 1.49 | 2.45 | 2.68 | 2.92 |
| 027 | — | N.T. | 1.97 | 1.49 | 2.68 | 2.45 | 2.21 |
| 028[e] | — | N.T. | — | — | 1.73 | 2.45 | 1.97 |
| 029 | — | N.T. | 0.8 | 1.49 | 2.45 | 2.45 | 2.45 |

[a]Not tested.
[b]Titer expressed as $\log_{10}$ of reciprocal of last dilution showing complete neutralization of cytopathic effect.
[c]Animals boosted at 28 days post-inoculation.
[d]Animals 026 and 027 received $1 \times 10^8$ pfu.
[e]Animals 028 and 029 received $1 \times 10^7$ pfu.

TABLE 7

Serological analysis of sera of rabbits inoculated with ALVAC-MV (vCP82)

| | Days post-inoculation | | | | | |
|---|---|---|---|---|---|---|
| Animal | 0 | 14 | 21 | 28[b] | 42 | 56 |
| Plaque reduction method | | | | | | |
| 063 | — | 1.9[a] | 2.8 | 1.6 | 2.2 | 2.2 |
| 064 | — | 2.2 | 2.5 | 2.8 | 3.1 | 2.8 |
| Microtiter neutralization method | | | | | | |
| 063 | — | 1.5[c] | 1.7 | 1.5 | 1.7 | |

[a]Titer expressed as $\log_{10}$ of reciprocal of last dilution showing a 50% reduction in plaque number as compared to pre-inoculation serum.
[b]Animals boosted at 28 days post-inoculation.
[c]Titer expressed as $\log_{10}$ of reciprocal of last dilution showing complete neutralization of cytophatic effect.

Previous studies have shown that an inactivated vaccine was associated with poor protective efficacy and an enhanced measles disease on re-exposure to the virus. Recipients of the inactivated vaccine demonstrated an absence of antibody to the fusion protein and it was proposed that the inactivation process had rendered the protein non-immunogenic (Norrby and Gollmar, 1975; Norrby et al., 1975). In addition, it has been shown for other paramyxoviruses that antibody to the F protein is able to inhibit cell to cell spread of virus in tissue culture while antibody to the hemagglutinin component is not (Merz et al., 1980).

It was therefore significant to demonstrate that animals inoculated with ALVAC-MV (vCP82) were able to induce antibody to the F component which was capable of blocking cell to cell transmission of measles virus. The results of this anti-fusion assay are shown in Table 8. Anti-fusion activity was evident in sera of both guinea-pigs and rabbits inoculated with ALVAC-MV (vCP82). The sera analyzed was taken two or three weeks after the boost inoculation. No anti-fusion activity could be detected in sera of rabbits inoculated with ALVAC parental virus.

TABLE 8

Analysis of sera of guinea pigs and rabbits inoculated with ALVAC-MV for anti-fusion activity

| Animal | Designation | Immunogen | Anti-Fusion Titer Pre-inoc. | Anti-Fusion Titer Post-Vacc. |
|---|---|---|---|---|
| Guinea-pig | 026 | ALVAC-MV | — | 2.4[a,b] |
|  | 027 | ALVAC-MV | — | 1.2 |
| Rabbit | 063 | ALVAC-MV | — | 1.8[c] |
|  | 064 | ALVAC-MV | — | 1.8 |
| Rabbit | W121 | ALVAC | — | — |
|  | W123 | ALVAC | — | — |

[a] Guinea pig sera tested at 7 weeks post-vaccination.
[b] Titer expressed as $\log_{10}$ of reciprocal of highest dilution showing complete inhibition of measles virus induced cell fusing activity.
[c] Rabbit sera test at 6 weeks post-vaccination.

In further tests to demonstrate the presence of antibody to both the MV hemagglutinin and MV fusion proteins in sera of animals inoculated with ALVAC-MV, immunoprecipitation experiments were performed. Sera of rabbits inoculated with ALVAC-MV was shown to specifically precipitate both the hemagglutinin and fusion proteins from radiolabelled lysates of Vero cells infected with Edmonston strain MV.

In a similar study, groups of guinea pigs, rabbits and mice were inoculated by the intra muscular route with ALVAC-MV, and their serological response to measles virus monitored using the hemagglutination-inhibition (HI) test. The serological response to canarypox virus was monitored by ELISA assay. In this study, five guinea pigs were inoculated with 5.5 $\log_{10}$ TCID$_{50}$, thirty mice were inoculated with 4.8 $\log_{10}$ TCID$_{50}$, and five rabbits were inoculated with 5.8 $\log_{10}$ TCID$_{50}$. All animals were re-inoculated at 28 days with an equivalent dose. Animals were bled at regular intervals and their response to measles virus assessed in an HI assay. The limit of detection in the HI assay corresponds to a $\log_{10}$ titer of 1 and it is considered that sero-positive (protected) children have a serum titer in the range of 1.6 to 2.8. The results of analysis are shown in Tables 9, 10 and 11.

Sera of mice were analyzed in groups of 5 animals (Table 9). All animals showed a primary response to canarypox virus which was boosted after the second inoculation. The mice did not show a response to MV after one inoculation. Three of the six groups showed titers within the protective range at 8 weeks post-inoculation. Similarly, all guinea-pigs (Table 10) showed a response to canarypox virus after one inoculation which was boosted after the second inoculation. Four of five animals developed anti-HI titers after one inoculation, one of these being in the protective range. One week after the second inoculation, the titers of all animals were in the protective range. These titers were maintained through 8 weeks post-inoculation when the experiment was concluded. All rabbits (Table 11) inoculated with ALVAC-MV (vCP82) responded serologically to canarypox inoculation. Four of five animals sero-converted to measles virus after one inoculation (one in the protective range). Serum titers of all animals were in the protective range one week after the second inoculation.

TABLE 9

Serological response of mice to inoculation with ALVAC-MV (vCP82)

| Mouse Group | Week post-inoculation 0 | 2 | 4 | 5 | 6 | 8 |
|---|---|---|---|---|---|---|
| Anti-canarypox response ELISA TITER | | | | | | |
| 1[a] | −0.009[b] | 0.364 | 0.193 | 1.821 | 1.616 | 1.123 |
| 2 | −0.026 | 0.047 | 0.240 | 1.739 | 1.963 | 1.986 |
| 3 | −0.006 | 0.148 | 0.641 | 1.860 | 1.861 | 1.947 |
| 4 | −0.005 | 0.130 | 0.451 | 1.506 | 1.937 | 1.124 |
| 5 |  | 0.687 | 0.542 |  |  |  |
| Mean | −0.012 | 0.275 | 0.413 | 1.732 | 1.844 | 1.395 |
| Anti-measles response HI TITER | | | | | | |
| 1 | <1[c] | <1 | <1 | <1 | 1 | 1 |
| 2 | <1 | <1 | <1 | 1 | 1.6 | 1.6 |
| 3 | <1 | <1 | 1 | 1 | 2.2 | 2.2 |
| 4 | <1 | <1 | <1 | 1.6 | 1 | 1.8 |
| 5 | <1 | <1 | <1 | 1.3 | 1.8 | 1.2 |
| Mean | — | — | 1 | 1.2 | 1.5 | 1.5 |

[a] Groups of five mice were exsanguinated and sera pooled.
[b] Optical density in an ELISA assay on sera at dilution of 1:800
[c] Limit of detection in HI test corresponds to a $\log_{10}$ titer of 1 i.e. 1:10 dilution. Titer expressed as $\log_{10}$ of reciprocal of highest dilution showing inhibition of hemagglutination.

TABLE 10

Serological response of guinea-pigs to inoculation with ALVAC-MV (vCP82)

| Guinea-pig | Week post-inoculation 0 | 2 | 4 | 5 | 6 | 8 |
|---|---|---|---|---|---|---|
| Anti-canarypox response ELISA TITER | | | | | | |
| 1 | 0.038[a] | 0.045 | 0.111 | 1.771 | 1.970 | 1.856 |
| 2 | 0.010 | 0.072 | 0.234 | 1.768 | 1.786 | 1.785 |
| 3 | −0.011 | 0.426 | 0.529 | 1.567 | 1.586 | 1.700 |
| 4 | 0.016 | 0.045 | 0.076 | 1.583 | 1.696 | 1.635 |
| 5 | −0.020 | 0.012 | 0.050 | 1.583 | 1.859 | 1.847 |
| Anti-measles response HI TITER | | | | | | |
| 1 | <1[b] | 1.18 | 1.90 | 3.11 | 3.41 | 3.11 |
| 2 | <1 | <1 | 1.00 | 2.20 | 2.20 | 2.08 |
| 3 | <1 | <1 | 1.18 | 2.51 | 2.68 | 2.98 |
| 4 | <1 | <1 | <1 | 1.60 | 1.90 | 1.90 |
| 5 | <1 | <1 | 1.30 | 1.90 | 2.20 | 2.20 |

[a] Optical density in an ELISA assay on serum at a 1:3200 dilution.
[b] Limit of detection in HI test corresponds to a $\log_{10}$ titer of 1 i.e. 1:10 dilution. Titer expressed as in legend to Table 9.

TABLE 11

Serological response of rabbits to inoculation with ALVAC-MV (vCP82)

| Rabbit | Week post-inoculation 0 | 2 | 4 | 5 | 6 | 8 |
|---|---|---|---|---|---|---|
| Anti-canarypox response ELISA TITER | | | | | | |
| 1[a] | −0.009[a] | 0.085 | 0.113 | 1.953 | 1.754 | 1.249 |
| 2 | −0.002 | 0.065 | 0.068 | 0.717 | 0.567 | 0.353 |
| 3 | −0.003 | 0.090 | 0.079 | 0.921 | 0.692 | 0.481 |

TABLE 11-continued

Serological response of rabbits to inoculation with ALVAC-MV (vCP82)

| Rabbit | Week post-inoculation | | | | | |
|---|---|---|---|---|---|---|
| | 0 | 2 | 4 | 5 | 6 | 8 |
| 4 | −0.005 | 0.034 | 0.068 | 1.558 | 1.324 | 1.076 |
| 5 | −0.003 | 0.072 | 0.092 | 1.785 | 1.226 | 0.710 |
| Anti-measles response HI TITER | | | | | | |
| 1 | <1[b] | <1 | 1.00 | 2.81 | 2.51 | 2.20 |
| 2 | <1 | <1 | <1 | 2.20 | 1.90 | 1.60 |
| 3 | <1 | <1 | 1.30 | 2.81 | 2.51 | 2.38 |
| 4 | <1 | 1.30 | 1.60 | 3.11 | 3.11 | 2.51 |
| 5 | <1 | 1.00 | 1.30 | 2.68 | 2.38 | 1.90 |

[a]Optical density in an ELISA assay on sera at a dilution of 1:1600.
[b]Limit of detection in HI test corresponds to a $log_{10}$ titer of 1 i.e. 1:10 dilution. Titer expressed as in legend to Table 9.

Results of Serological Analysis of Sera of Squirrel Monkeys Inoculated with ALVAC-MV (vCP82): Influence of Prior Exposure to Poxvirus on Induction of a Measles Virus Specific Immune Response Nine squirrel monkeys (*Saimiri sciureus*) were inoculated with ALVAC-MV (vCP82). All monkeys were naive to measles virus. Seven of the monkeys had prior exposure to vaccinia virus and/or canarypox virus. The previous immunization history is shown in Table 12. All monkeys were inoculated with one dose of 5.8 $log_{10}$ pfu by the subcutaneous route. Four of the animals (#39, 42, 53 and 58) were re-inoculated with an equivalent dose fifteen weeks after the primary inoculation. Anti-measles antibody was measured in the HI test. The results are shown in Table 12.

After the first inoculation, two of the nine monkeys showed a low response to inoculation with ALVAC-MV. After the second inoculation, the four monkeys re-inoculated all sero-converted with significant antibody titers in the range required for protective immunity. The titers achieved were equivalent whether the monkey had prior exposure to vaccinia virus and ALVAC or no prior poxvirus exposure.

TABLE 12

Inoculation of squirrel monkeys with ALVAC-MV (vCP82): Immune response in the face of pre-existing ALVAC immunity.

| Monkey # | Previous Immunity to Poxviruses | Anti-Measles Primary[a] | HI response Boost[b] |
|---|---|---|---|
| 36 | VV, ALVAC | <1 | N.B. |
| 37 | VV, ALVAC-RG | <1 | N.B. |
| 39 | VV, ALVAC-RG, CP-FeLV | 1 | 2.2 |
| 40 | VV, CP-FeLV | <1 | N.B. |
| 42 | None | <1 | 2.2 |
| 52 | ALVAC | <1 | N.B. |
| 53 | ALVAC-RG, ALVAC-RG | <1 | 1.6 |
| 56 | CP-FeLV | <1 | N.B. |
| 58 | None | 1 | 2.2 |

VV: Vaccinia virus, Copenhagen strain
ALVAC-RG: ALVAC recombinant expressing rabies G gene
CP-FeLV: Canarypox recombinant expressing FeLV env gene
NB: Not boosted
[a]Animals received 5.8 $log_{10}$ pfu by S.C. route.
[b]Animals 39, 42, 52 and 53 were boosted with an identical dose 15 weeks after the first inoculation.

EXAMPLE 15

Attenuated Vaccinia Vaccine Strain NYVAC

To develop a new vaccinia vaccine strain, the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al. (1990a,b).

The deletion loci were also engineered as recipient loci for the insertion of foreign genes.

The regions sequentially deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L–K1L) vP804; and
(6) large subunit, ribonucleotide reductase (I4L) vP866 (NYVAC).

DNA Cloning and Synthesis

Plasmids were constructed, screened and grown by standard procedures (Maniatis et al., 1986; Perkus et al., 1985; Piccini et al., 1987). Restriction endonucleases were obtained from GIBCO/BRL, Gaithersburg, Md., New England Biolabs, Beverly, Mass.; and Boehringer Mannheim Biochemicals, Indianapolis, Ind. Klenow fragment of *E. coli* polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection

The origins and conditions of cultivation of the Copenhagen strain of vaccinia virus has been previously described (Guo et al., 1989). Generation of recombinant virus by recombination, in situ hybridization of nitrocellulose filters and screening for Beta-galactosidase activity are as previously described (Panicali et al., 1982; Perkus et al., 1989).

Construction of Plasmid pSD460 for Deletion of Thymidine Kinase Gene (J2R)

Figure 9:
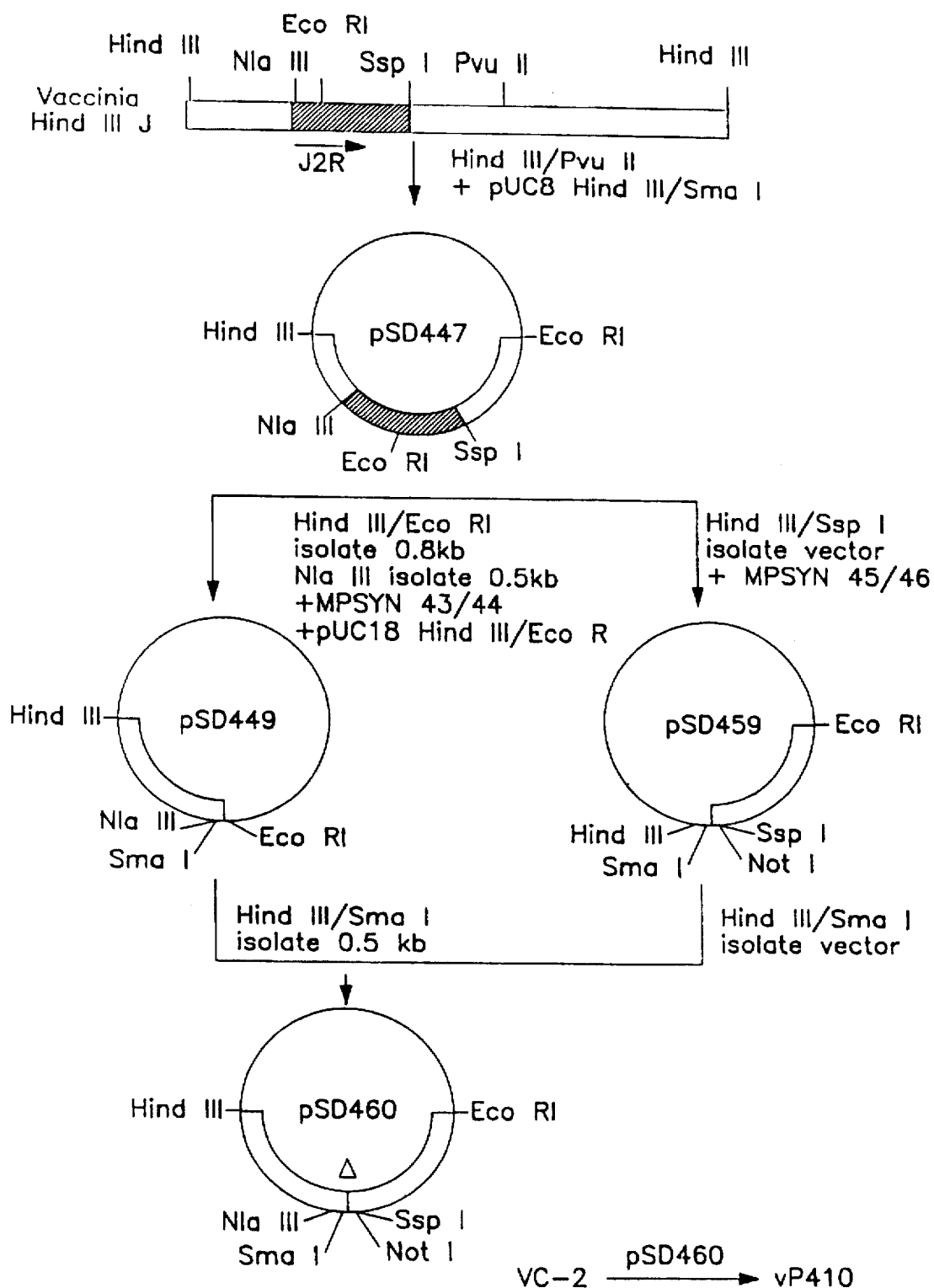
FIG. 9 schematically shows a method for the construction of plasmid pSD460 for deletion of thymidine kinase gene and generation of recombinant vaccinia virus vP410.

Referring now to FIG. 9, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC:8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 9.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:17/SEQ ID NO:18)

```
                          SmaI
MPSYN43  5'      TAATTAACTAGCTACCCGGG              3'
MPSYN44  3'  GTACATTAATTGATCGATGGGCCCTTAA          5'
             NlaIII                        EcoRI
``` were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequence, pSD447 was cut with SspI (partial) within vaccinia sequence and HindIII at the indicated by a triangle. The remaining B13R coding sequences in pSD477 were removed by digestion with ClaI/HnaI, and the resulting vector fragment was ligated with annealed synthetic oligonucleotides SD22mer/SD20mer (SEQ ID NO:22/SEQ ID NO:23)

```
             ClaI           BamHI  HpaI
SD22mer  5'  CGATTACTATGAAGGATCCGTT   3'
SD20mer  3'      TAATGATACTTCCTAGGCAA 5'
``` generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating

```
         HindIII   SmaI
MPSYN45  5'   AGCTTCCCGGGTAAGTAATACGTCAAGGAGAAAACGAA
MPSYN46  3'       AGGGCCCATTCATTATGCAGTTCCTCTTTTGCTT NotI                 SspI
         ACGATCTGTAGTTAGCGGCCGCCTAATTAACTAAT  3'  MPSYN45
         TGCTAGACATCAATCGCCGGCGGATTAATTGATTA  5'  MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$p labeled probe was synthesized by primer extension using MPSYN45 (SEQ ID NO:19) as template and the complementary 20mer oligonucleotide MPSYN47 (SEQ ID NO:21) (5'-TTAGTTAATTAGGCGGCCGC-3') as primer. Recombinant virus vP410 was identified by plaque hybridization.

Construction of Plasmid pSD486 for Deletion of Hemorrhagic Region (B13R+B14R)

Figure 10:
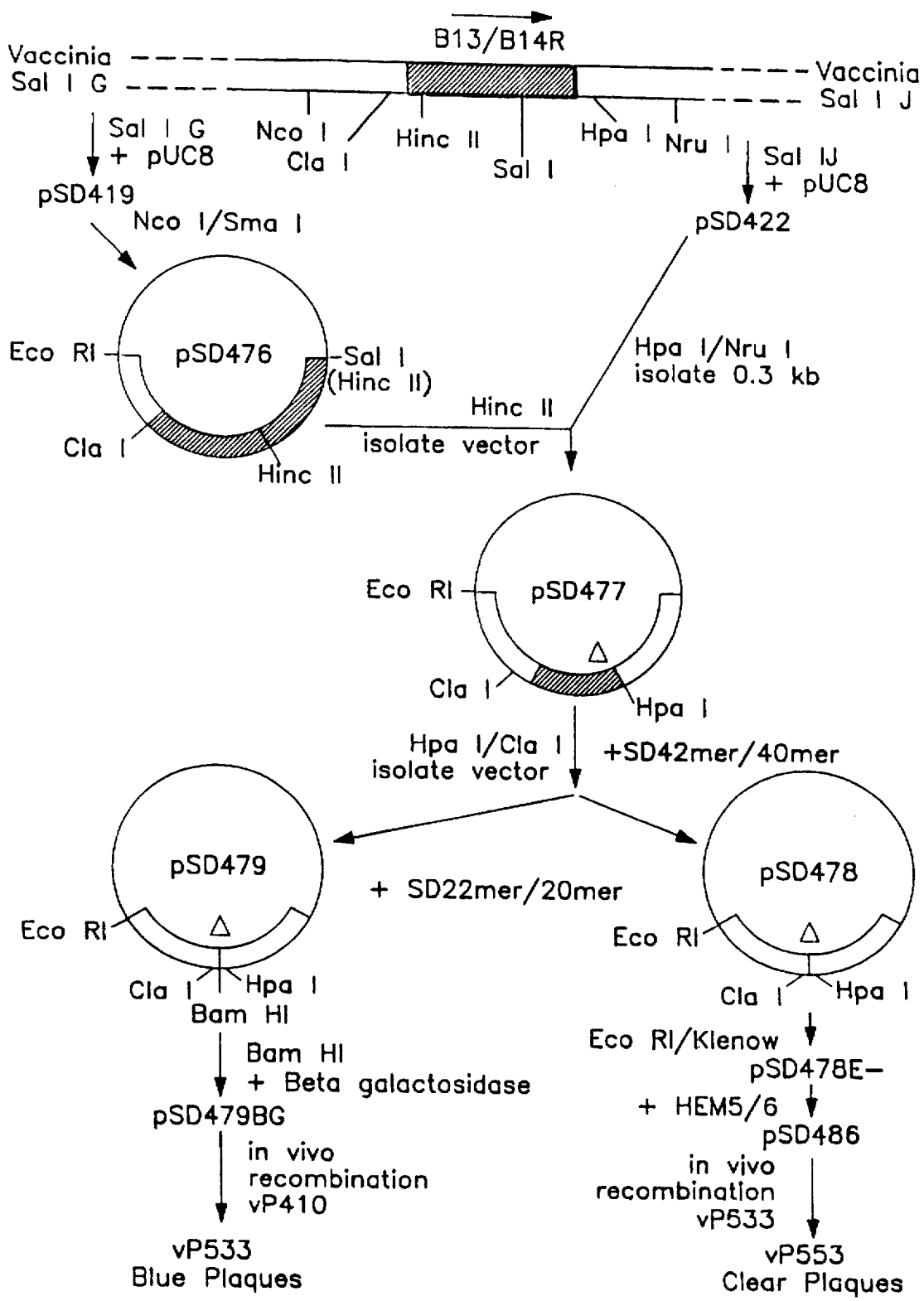
FIG. 10 schematically shows a method for the construction of plasmid pSD486 for deletion of hemorrhagic region and generation of recombinant vaccinia virus vP553.

Referring now to FIG. 10, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8.

pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R-B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:24/SEQ ID NO:25)

```
             ClaI            SacI           XhoI              HpaI
SD42mer  5'  CGATTACTAGATCTGAGCTCCCCGGGCTCGAGGGATCCGTT   3'
SD40mer  3'      TAATGATCTAGACTCGAGGGGCCCGAGCTCCCTAGGCAA 5'
             BglII            SmaI          BamHI
```

To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 10.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E⁻. pSD478E⁻ was digested with BamHI and EaI and ligated with annealed synthetic oligonucleotides HEM5/HEM6 (SEQ ID NO:26/SEQ ID NO:27)

```
          BamHI  EcoRI  HpaI
HEM5  5'  GATCCGAATTCTAGCT   3'
HEM6  3'      GCTTAAGATCGA   5'
``` generating plasmid pSD486. pSD486 was used as donor plasmid for recombination with recombinant vaccinia virus vP533, generating vP553, which was isolated as a clear plaque in the presence of X-gal.

Construction of Plasmid pMP494Δ for Deletion of ATI Region (A26L)

Figure 11:
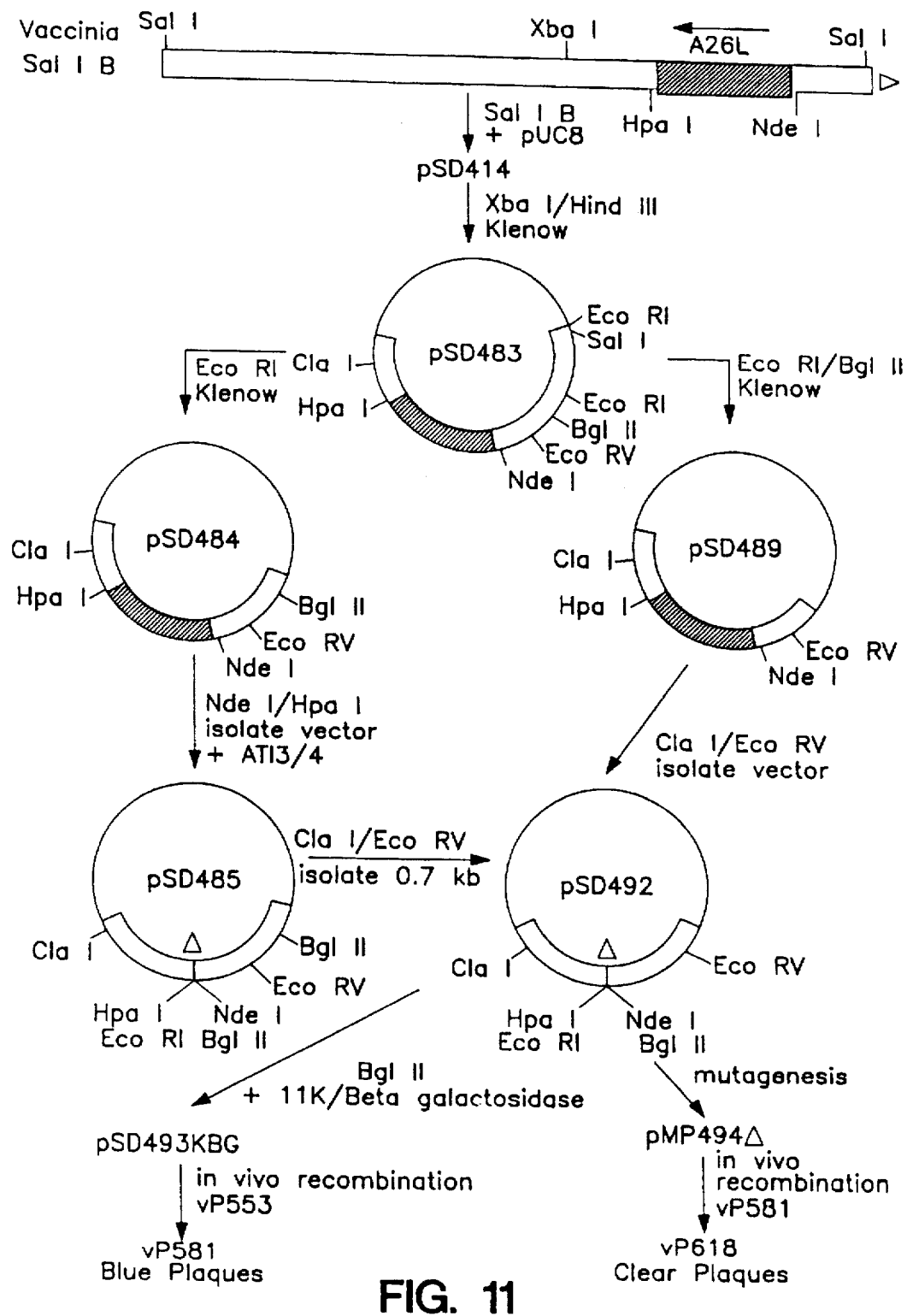
FIG. 11 schematically shows a method for the construction of plasmid pMP494Δ for deletion of ATI region and generation of recombinant vaccinia virus vP618.

Referring now to FIG. 11, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:28/SEQ ID NO:29)

A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:30) (5'-AAAATGGGCGTGGATTGTTAACTTTATATA-ACTTATTTTTTGAATATAC-3'). In the resulting plasmid, pMP494Δ, vaccinia DNA encompassing positions [:L37, 889–138,937], including the entire A26L ORF is deleted. Recombination between the pMP494A and the Beta-galactosidase containing vaccinia recombinant, vP581, resulted in vaccinia deletion mutant vP618, which was isolated as a clear plaque in the presence of X-gal.

Construction of Plasmid pSD467 for Deletion of Hemagglutinin Gene (AS6R)

Figure 12:
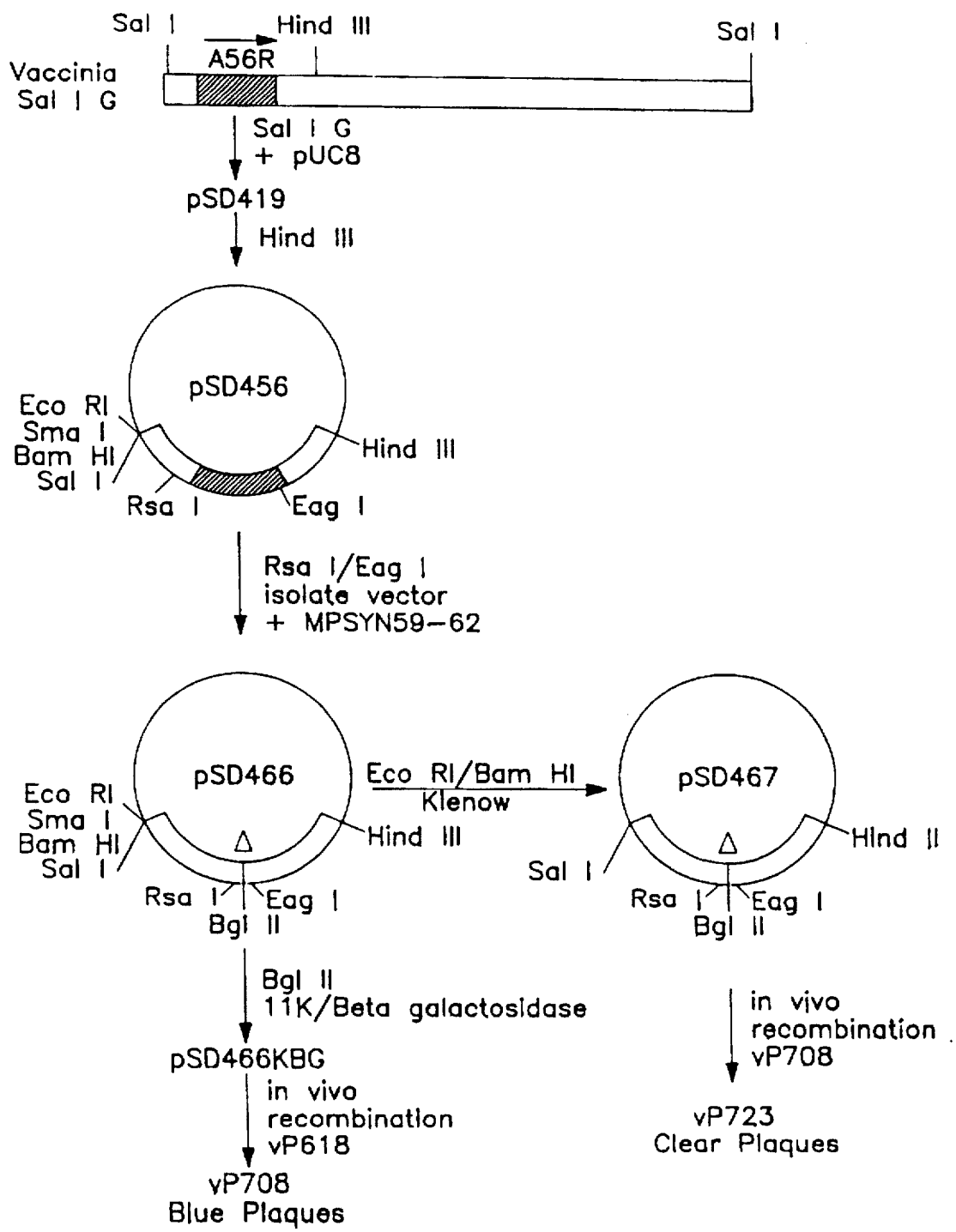
FIG. 12 schematically shows a method for the construction of plasmid pSD467 for deletion of hemagglutinin gene and generation of recombinant vaccinia virus vP723.

Referring now to FIG. 12, vaccinia SalI G restriction fragment (pos. 160,744–173,351) crosses the HindIII A/B

```
           NdeI
ATI3  5' TATGAGTAACTTAACTCTTTTGTTAATTAAAAGTATATTCAAAAAATAAGT
ATI4  3'     ACTCATTGAATTGAGAAAACAATTAATTTTCATATAAGTTTTTTATTCA

BglII   EcoRI   HpaI
      TATATAAATAGATCTGAATTCGTT  3' ATI3
      ATATATTTATCTAGACTTAAGCAA  5' ATI4
``` reconstructing the region upstream from A26L and replacing the A26L ORF with a short polylinker region containing the restriction sites BglII, EcoRI and HpaI, aLs indicated above. The resulting plasmid was designated pSD485. Since the BglII and EcoRI sites in the polylinker region of pSD485 are not unique, unwanted BalII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BalII and EcoRI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BII site of pSD492, forming pSD493KBG. Plasmid pSD493KBG was used in recombination with rescuing virus vP553. Recombinant vaccinia virus, vP581, containing Beta-galactosidase in the junction (pose 162,539). pSD419 contains vaccinia SalI G cloned into pUC8. The direction of transcription for the hemagglutinin (HA) gene is indicated by an arrow in FIG. 12. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia seqences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:31), MPSY62 (SEQ ID NO:32), MPSYN60 (SEQ ID NO:33), and MPSYN 61 (SEQ ID NO:34)

```
(SEQ ID NO:34)
              RsaI
MPSYN59  5' ACACGAATGATTTTCTAAAGTATTTGGAAAGTTTTATAGGTAGTTGATAGA-
MPSYN62  3' TGTGCTTACTAAAAGATTTCATAAACCTTTCAAAATATCCATCAACTATCT 5'

MPSYN59   - ACAAAATACATAATTT 3'

BglII
MPSYN60  5'                  TGTAAAAATAAATCACTTTTTATACTAAGATCT-
MPSYN61  3' TGTTTTATGTATTAAAACATTTTTATTTAGTGAAAAATATGATTCTAGA-

SmaI    PstI   EagI
MPSYN60   - CCCGGGCTGCAGC        3'
MPSYN61   - GGGCCCGACGTCGCCGG 5'
``` reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,0533. The site of the deletion in pSD466 is indicated by a triangle in FIG. 12.

A 3kb BglII/tanHI (partial) cassette containing the *E. coli* Beta-galactosidase gene (Shapira et al., 1983) under the control of the vaccinia 11 kDa promoter (Bertholet et al., 1985; Guo et al., 1989) was inserted into the BglII site of pSD466, forzing pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of *E. coli* polymerase and ligation. Recombination between vP708 and pSD467 resulted in recombinant vaccinia deletion mutant, vP723, which was isolated as a clear plaque in the presence of X-gal.

Construction of Plasmid pMPCSK1Δ for Deletion of Open Reading Frames [C7L–K1L]

Figure 13:
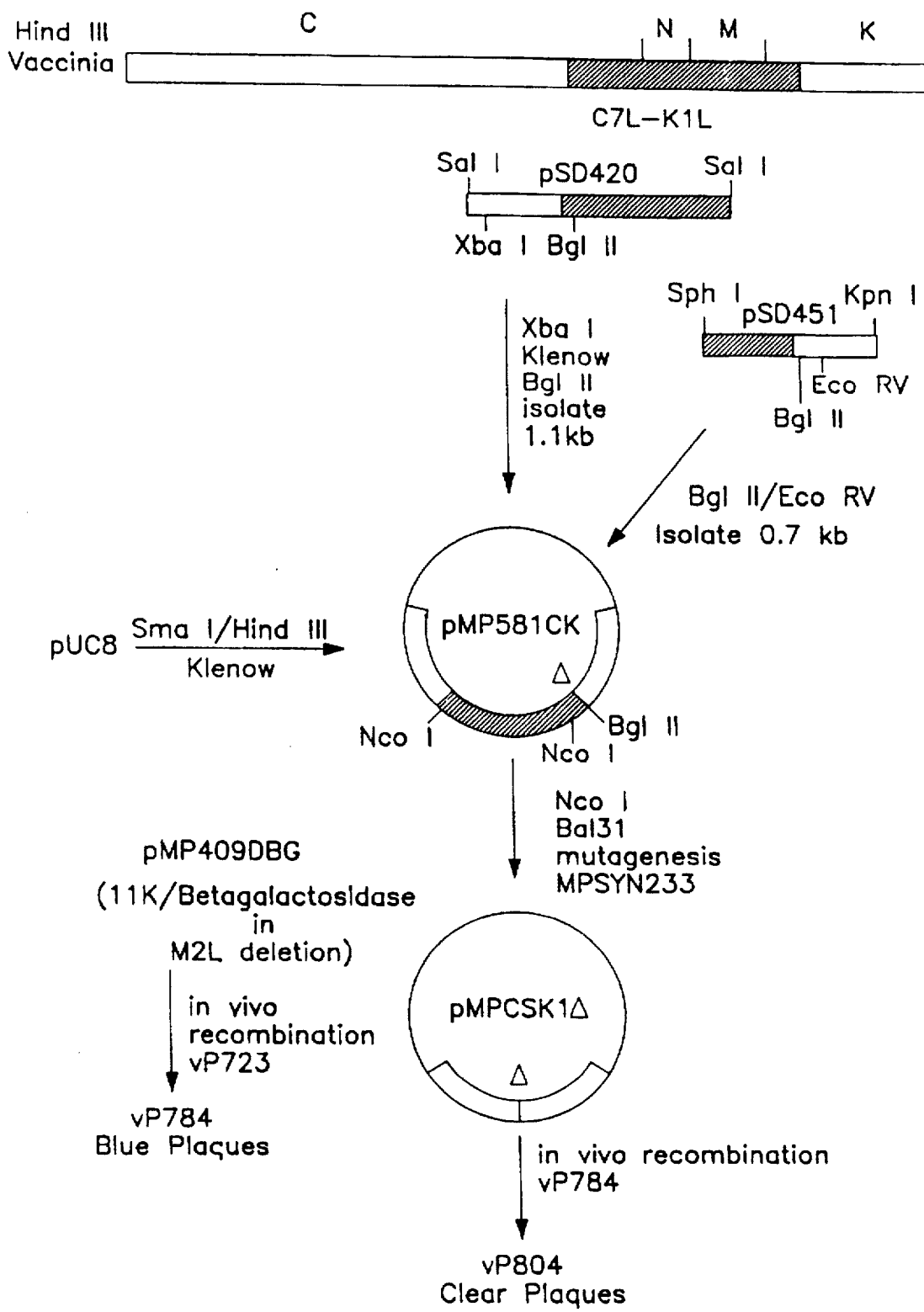
FIG. 13 schematically shows a method for the construction of plasmid pMPCSK1Δ for deletion of gene cluster [C7L–K1L] and generation of recombinant vaccinia virus vP804.

Referring now to FIG. 13, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, *E. coli* Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide flanking arm consisting of vaccinia HindIII K sequences was obtained by digestion of pSD451 with BglII (pos. 29,062) and EcoRV (pos. 29,778). The resulting plasmid, pMP581CK is deleted for vacci.nia sequences between the BglII site (pos. 19,706) in HindIII C and the BglII site (pos. 29,062) in HindIII K. The site of the deletion of vaccinia sequences in plasmid pMP581CK is indicated by a triangle in FIG. 13.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:36) 5'-TGTCATTTAACACTA-TACTCATATTAATAAAAATAATATTTATT-3'. The resulting plasmid, pMPCSK1Δ, is deleted for vaccinia sequences positions 18,805–29,108, encompassing 12 vaccinia open reading frames [C7L - K1L]. Recombination between pMPCSK1Δ and the Betat-galactosidase containing vaccinia recombinant, vP784, resulted in vaccinia deletion mutant, vP804, which was isolated as a clear plaque in the presence of X-gal.

Construction of Plasmid pSD548 for Deletioni of Large Subunit, Ribonucleotide Reductase (I4L)

Figure 14:
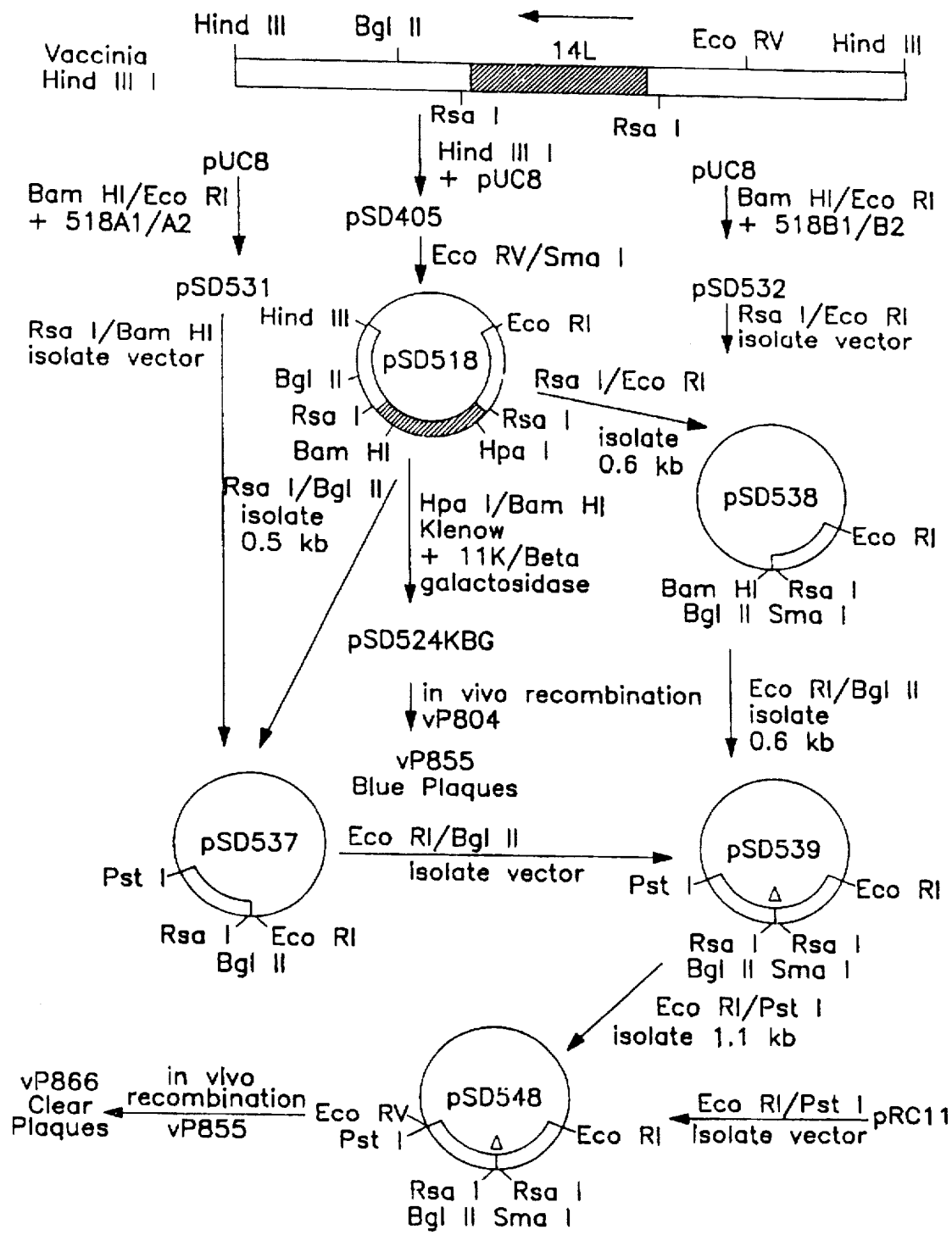
FIG. 14 schematically shows a method for the construction of plasmid pSD548 for deletion of large subunit, ribonucleotide reductase and generation of recombinant vaccinia virus vP866 (NYVAC), and FIG. 15 schematically shows a method for the construction of plasmid pRW857 used to derive recombinant NYVAC virus vP913 co-expressing the MV hemagglutinin and fusion genes.

Referring now to FIG. 14, plasmici pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65, 059. Direction of transcription for I4L is indicated by an arrow in FIG. 14. To obtain a vector plasmid fragment deleted for a portion of the I4L coding sequences, pSD518 was digested with BamHI (pos. 65,381) and HpaI (pos. 67,001) and blunt ended using Klenow fragment of *E. coli* polymerase. This 4.8 kb vector fragment was ligated with a 3.2 kb SmaI cassette containing the *E. coli* Beta- BglII
MPSYN82 (SEQ ID NO:35) 5' TTTCTGTATATTTGCACCAATTTAGATCTTACTCAAAA
TATGTAACAATA 3'

The resulting plasmid, pMP409D, contains a unique BglII site inserted into the M2L deletion locus as indicated above. A 3.2 kb BamHI (partial)/BglII cassette containing the *E. coli* Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of *E. coli* polymerase. The left flanking arm consisting of vaccinia HindIII C sequences was obtained by digestion of pSD420 with XbaI (pos. 18,628) followed by blunt ending with Klenow fragment of *E. coli* polymerase and digestion with BglII (pos. 19,706). The right galactosidase gene (Shapira et al., 1983) under the control of the vaccinia 11 kDa promoter (Bertholet et al., 1985; Perkus et al., 1990), resulting in plasmid PSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 14.

To construct a vector plasmid to accept the left vaccinia flanking arm, pUC8 was cut with BamHI/EcoRI and ligated with annealed synthetic oligonucleotides 518A1/518A2

(SEQ ID NO:37/SEQ ID NO:38)

```
        BamHI    RsaI
518A1 5' GATCCTGAGTACTTTGTAATATAATGATATATATTTTCACTTTATCTCAT
518A2 3'        GACTCATGAAACATTATATTACTATATATAAAAGTGAAATAGAGTA

BglII        EcoRI
         TTGAGAATAAAAAGATCTTAGG          3' 518A1
         AACTCTTATTTTTCTAGAATCCTTAA      5' 518A2
``` forming plasmid pSD531. pSD531 was cut with RsaI (partial) and BamHI and a 2.7 kb vector fragment isolated. pSD518 was cut with BglII (pos. 64,459)/ RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 tion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

(SEQ ID NO:39/SEQ ID NO:40)

```
        BamHI BglII   SmaI
518B1 5' GATCCAGATCTCCCGGGAAAAAAATTATTTAACTTTTCATTAATAGGGATTT
518B2 3'     GTCTAGAGGGCCCTTTTTTTAATAAATTGAAAAGTAATTATCCCTAAA

RsaI      EcoRI
         GACGTATGTAGCGTACTAGG            3' 518B1
         CTGCATACTACGCATGATCCTTAA        5' 518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 14. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, at pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six dele-

EXAMPLE 16

Construction of NYVAC-MV Recombinant Expressing Measles Fushios and Hemagglutinin Glycoprotiens cDNA copies of the sequences encoding the HA and F proteins of measles virus MV (Edmonston strain) were inserted into NYVAC to create a double recombinant designated NYVAC-MV (vP913). The recombinant authentically expressed both measles glycoproteins on the surface of infected cells. Immunoprecipitation analysis demonstrated correct processing of both F and HA glycoproteins. The recombinant was also shown to induce syncytia formation.

Cells and Viruses

The rescuing virus used in the production of NYVAC-MV was the modified Copenhagen strain of vaccinia virus designated NYVAC. All viruses were grown and titered on Vero cell monolayers.

Plasmid Construction

Figure 15:
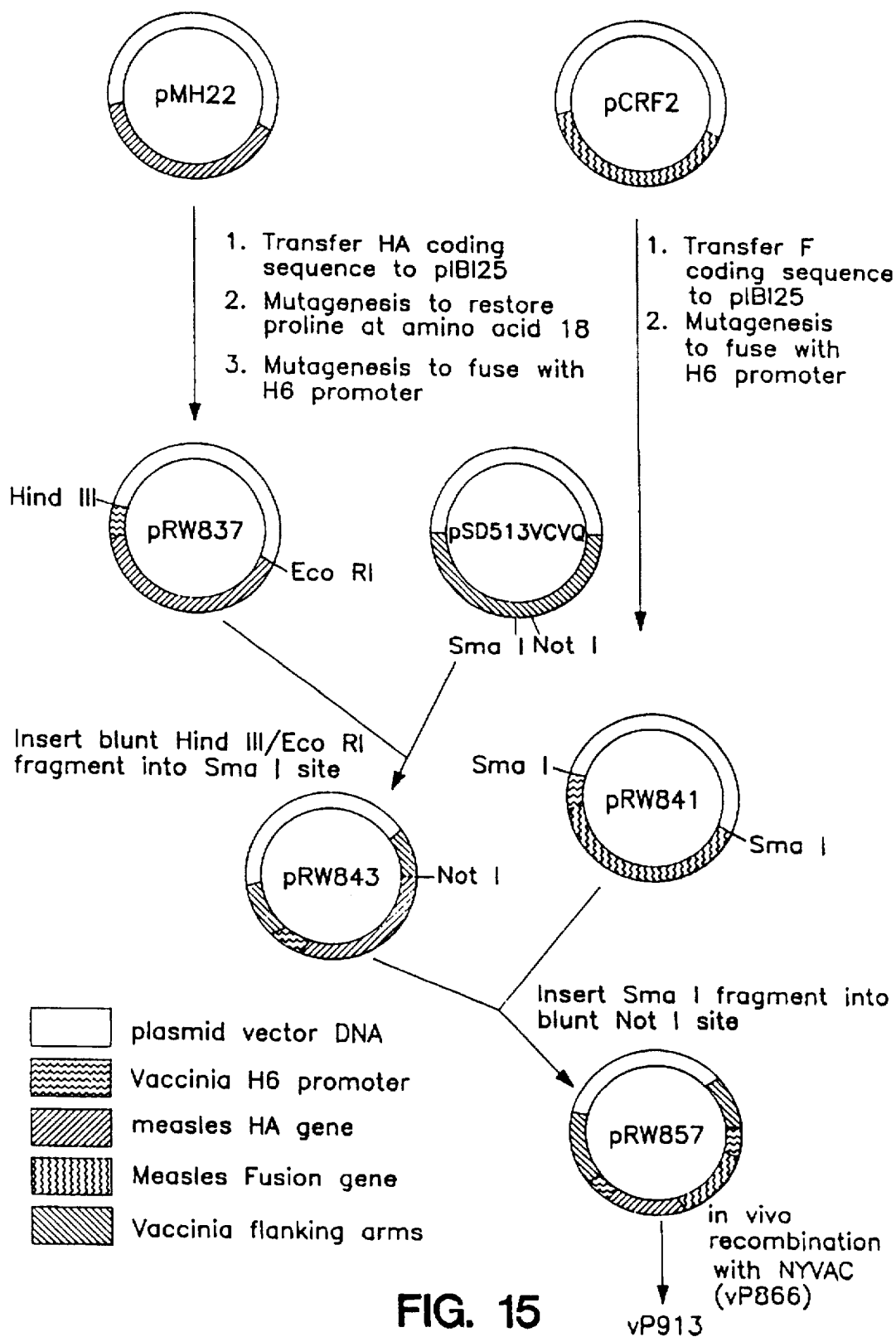

Referring now to FIG. 15 and Taylor et al. (1991), plasmid pSPM2LHA contains the entire measles HA gene linked in a precise ATG to ATG configuration with the vaccinia virus H6 promoter which has been previously described (Taylor et al., 1988a,b; Guo et al., 1989; Perkus et al., 1989). A 1.8kpb EcoRV/SmaI fragment containing the 3' most 24 bp of the H6 promoter fused in a precise ATG:ATG configuration with the HA gene lacking the 3' most 26 bp was isolated from pSPM2LHA. This fragment was used to replace the 1.8 kbp EcoRV/SmaI fragment of pSPMHA11 (Taylor et al., 1991) to generate pRW803. Plasmid pRWBO3 contains the entire H6 promoter linked precisely to the entire measles HA gene.

Plasmid pSD513VCVQ was derived from plasmid pSD460 by the addition of polylinker sequences. Plasmid pSD460 was derived to enable deletion of the thymidine kinase gene from vaccinia virus (FIG. 9).

To insert the measles virus F gene into the HA insertion plasmid, manipulations were performed on pSPHMF7. Plasmid pSPHMF7 (Taylor et al., 1991) contains the measles F gene juxtaposed 3' to the previously described vaccinia virus H6 promoter. In order to attain a perfect ATG for ATG configuration and remove intervening sequences between the 3' end of the promoter and the ATG of the measles F gene oligonucleotide directed mutagenesis was performed using oligonucleotide SPMAD (SEQ ID NO:41).

SPMAD: 5'-TATCCGTTAAGTTTGTATCGTAATGGGT-CTCAAGGTGAACGTCT-3'

The resultant plasmid was designated pSPMF75M20.

The plasmid pSPMF75M20 which contains the measles F gene now linked in a precise ATG for ATG configuration with the H6 promoter was digested with NruI and EagI. The resulting 1.7 kbp blunt ended fragment containing the 3' most 27 bp of the H6 promoter and the entire fusion gene was isolated and inserted into an intermediate plasmid pRW823 which had been digested with NruI and XbaI and blunt ended. The resultant plasmid pRW841 contains the H6 promoter linked to the measles F gene in the pIBI25 plasmid vector (IBI, New Haven, Conn.). The H6/measles F cassette was excised from pRW841 by digestion with SmaI and the resulting 1.8 kb fragment was inserted into pRW843 (containing the measles HA gene). Plasmid pRW843 was first digested with NotI and blunt-ended with Klenow fragment of *E. coli* DNA polymerase in the presence of 2mM dNTPs. The resulting plasmid, pRW857, therefore contains the measles virus F and HA genes linked in a tail to tail configuration. Both genes are linked to the vaccinia virus H6 promoter.

Development of NYVAC-MV

Plasmid pRW857 was transfected into NYVAC (vP866) infected Vero cells by using the calcium phosphate precipitation method previously described (Panicali et al., 1982; Piccini et ale, 1987). Positive plaques were selected on the basis of in situ plaque hybridization to specific MV F and HA radiolabeled probes and subjected to 6 sequential rounds of plaque purification until a pure population was achieved. One representative plaque was then amplified and the resulting recombinant was designated NYVAC-MV (vP913).

Immunofluorescence

Indirect immunofluorescence was performed as previously described (Taylor et al., 1990). Mono-specific reagents used were sera generated by inoculation of rabbits with canarypox recombinants expressing either the measles F or HA genes.

Immunoprecipitation

Immunoprecipitation reactions were performed as previously described (Taylor et al., 1990) using a guinea-pig anti measles serum (Whittaker M. A. Bioproducts, Walkersville, Md.).

Cell Fusion Experiments

Vero cell monolayers in 60 mm dishes were inoculated at a multiplicity of 1 pfu per cell with parental or recombinant viruses. After 1 h absorption at 37° C. the inoculum was removed, the overlay medium replaced and the dishes inoculated overnight at 37° C. At 20 h post-infection, dishes were examined.

In order to determine that the expression products of both measles virus F and HA genes were presented on the infected cell surface, indirect immunofluorescence analysis was performed using mono-specific sera generated in rabbits against canarypox recombinants expressing either the measles F or HA genes. The results indicated that both F and HA gene products were expressed on the infected cell surface, as demonstrated by strong surface fluorescence with both mono-specific sera. No background staining was evident with either sera on cells inoculated with the parental NYVAC strain, nor was there cross-reactive staining when mono-specific sera were tested against vaccinia single recombinants expressing either the HA or F gene.

In order to demonstrate that the proteins expressed by NYVAC-MV were immunoreactive with measles virus specific sera and were authentically processed in the infected cell, immunoprecipitation analysis was performed. Vero cell monolayers were inoculated at a multiplicity of 10 pfu/cell of parental or recombinant viruses in the presence of $^{35}$S-methionine. Immunoprecipitation analysis revealed a HA glycoprotein of approximately 76 kDa and the cleaved fusion products $F_1$ and $F_2$ with molecular weights of 44 kDa and 23 kDa, respectively. No measles specific products were detected in uninfected Vero cells or Vero cells infected with the parental NYVAC virus.

A characteristic of MV cytopathology is the formation of syncytia which arise by fusion of infected cells with surrounding infected or uninfected cells followed by migration of the nuclei toward the center of the syncytium (Norrby et al., 1982). This has been shown to be an important method of viral spread, which for Paramyxoviruses, can occur in the presence of HA-specific virus neutralizing antibody (Merz et al., 1980). In order to determine that the MV proteins expressed in vaccinia virus were functionally active, Vero cell monolayers were inoculated with NYVAC and NYVAC-MV and observed for cytopathic effects. Strong cell fusing activity was evident in NYVAC-MV infected Vero cells at approximately 18 hours post infection. No cell fusing activity was evident in cells infected with parental NYVAC.

Results of Serological Analysis of Sera of Rabbits Inoculated with NYVAC-MV (vP913)

In this study, two rabbits were inoculated with 1×10$^8$ pfu of NYVAC-MV (vP913) by the subcutaneous route. At 28 days, animals were boosted with an equivalent dose. Serial bleeds were analyzed for MV neutralizing activity using the plaque reduction method. The results are shown in Table 13. The results indicate that neither rabbit responded to the initial inoculation of NYVAC-MV. However, the sharply rising response after the second inoculation indicates that the animals were primed. Both animals achieved neutralizing antibody titers in the protective range.

The in vivo analysis of immunogenicity of ALVAC-MV (vCP82) shown in Example 14 indicates that on inoculation of a range of species, the recombinant is able to induce a serological response which is measurable in standard serological tests. The titers achieved are in the range required for protection from disease. Inoculation of NYVAC-MV (vP913) into rabbits similarly induces a level of measles virus neutralizing antibody which would be protective.

TABLE 13

Anti-measles neutralizing antibody titers (log$_{10}$) in sera of rabbits inoculated with NYVAC-MV (vP913)

| Animal | | W0 | W2 | W4[c] | W5 | W6 | W7 |
|---|---|---|---|---|---|---|---|
| Rabbit[a] | A116 | <1 | <1 | <1 | 2.8[b] | 2.2 | 2.2 |
| | A117 | <1 | <1 | <1 | 1.9 | 1.9 | 1.9 |

[a]Rabbits received 8.0 log$_{10}$ pfu of NYVAC-MV (vP913) by S.C. route.
[b]Titer expressed as log$_{10}$ of reciprocal of last dilution showing a 50% reduction in plaque number as compared to pre-inoculation serum.
[c]Animals were re-inoculated at 28 days.

REFERENCES

1. Adams, J. M., and D. T. Imagawa, Proc. Soc. Exper. Biol. Med. 96, 240–244 (1957).

2. Albrecht, P., K. Herrman, and G. R. Burns, J. Virol. Methods 3, 251–260 (1981).
3. Alkhatib, G., and D. Briedis, Virology 150, 479–490 (1986).
4. Alkhatib, G., C. Richardson, and S-H. Shen, Virology 175, 262–270 (1990).
5. Appel, M. J. G., and O. R. Jones, Proc. Soc. Exp. Biol. Med. 126, 571–574 (1967).
6. Appel, M. J. G., and D. S. Robson, Am. J. Vet. Res. 34, 1459–1463 (1973).
7. Avery, R. J., and J. Niven, Infect. Imnmun. 26, 795–801 (1979).
8. Baker, J. A., B. E. Sheffy, D. S. Robson, J. Gilmartin, Cornell Vet (USA) 56, 588–594 (1966).
9. Bertholet, C., R. Drillien, and R. Wittek, Proc. Natl. Acad. Sci. USA 82, 2096–2100 (1985).
10. Bestetti, G., R. Fatzer, and R. Frankhauser, Acta Neuropathol. 43, 69–75 (1978).
11. Black, F. L., L. L.Berman, M. Libel, C. A. Reichelt, F. de P. Pinheiro, A. T. da Rosa, F. Figuera, and E. S.Gonzales, Bull. W. H. O. 62, 315–319 (1984).
12. Bush, M., R. J. Montali, D. Brownstein, A. E. James, Jr., and M. J. G. Appel, J. Am. Vet. Med. Assoc. 169, 959–960 (1976).
13. Carpenter, J. W., M. J. G. Appel, R. C. Erickson, and M. N. Novilla, J. Am. Vet. Med. Assoc. 169, 961–964 (1976).
14. Choppin, P. W., C. D. Richardson, D. C. Mferz, W. W. Hall, and A. Scheid, J. Infect. Dis. 143, 352–363 (1981).
15. Clewell, D. B., J. Bacteriol. 110, 667–676 (1972).
16. Clewell, D. B., and D. R. Helinski, Proc. Natl. Acad. Sci. USA 62, 1159–1166 (1969).
17. Colinas, R. J., R. C. Condit, and E. Paoletti, Virus Research 18, 49–70 (1990).
18. DeLay, P. D., S. S. Stone, D. T. Karzon, S. Katz, and J. Enders, Am. J. Vet. Res. 26, 1359–1373 (1965).
19. Diallo, A., Vet. Micro. 23, 155–163 (1990).
20. Dowling, P. C., B. M. Blumberg, J. Menonna, J. E. Adamus, P. Cook, J. C. Crowley, D. Kolakofsky, and S. D. Cook, J. Gen. Virol. 67, 1987–1992 (1986).
21. Drillien, R., D. Spehner, A. Kirn, P. Giraudon, R. Buckland, F. Wild, and J. P. Lecocq, Proc. Natl. Acadl. Sci. USA 85, 1252–1256 (1988).
22. Engelke, D. R., P. A. Hoener, and F. S. Collins, Proc. Natl. Acad. Sci. USA 85, 544–548 (1988).
23. Fenner, F., P. A. Bachmann, E. P. J. Gibbs, F. A. Murphy, M. J. Studdert, and D. O. White, In Veterinary Virology, ed. F. Fenner, (Academic Press, Inc., New York) pp. 485–503 (1987).
24. Gillespie, J. H., and D. T. Karzon, Proc. Soc. Exp. Biol Med. 105, 547–551 (1960).
25. Giraudon, P., Ch. Gerald, and T. F. Wild, Intervirology 21, 110–120 (1984).
26. Goebel, S. J., G. P. Johnson, M. E. Perkus, S. W. Davis, J. P. Winslow, and E. Paoletti, Virology 179, 247–266 (1990a).
27. Goebel, S. J., G. P. Johnson, M. E. Perkus, S. W. Davis, J. P. Winslow, and E. Paoletti, Virology 179, 517–563 (1990b).
28. Graves, M. C., S. M. Silver, and P. W. Choppin, Virology 86, 254–263 (1978).
29. Guo, P., S. Goebel, S. Davis, M. E. Perkus, B. Languet, P. Desmettre, G. Allen, and E. Paoletti, J. Virol. 63, 4189–4198 (1989).
30. Guo, P., S. Goebel, S. Davis, M. E. Perkus, J. Taylor, E. Norton, G. Allen, B. Languet, P. Desmettre, and E. Paoletti, J. Virol. 64, 2399–2406 (1990).
31. Hall, W. W., R. A. Lamb, and P. W. Choppin, Virology 100, 433–449 (1980).
32. Hartley, W. J., Vet. Path. 11, 301–312 (1974).
33. Imagawa, D. T., P. Goret, and J. M. Adams, Proc. Natl. Acad. Sci. USA 46, 1119–1123 (1960).
34. Karzon, D. T., Pediatrics 16, 809–818 (1955).
35. Karzon, D. T., Annals of the N.Y. Academy of Sci. 101, 527–539 (1962).
36. Kazacos, K. R., H. L. Thacker, H. L. Shivaprasad, and P. P. Burger, J. Am. Vet. Med. Assoc. 179, 1166–1169 (1981).
37. Kingsbury, D. W., M. A. Bratt, P. W. Choppin, R. P. Hanson, T. Hosaka, V. ter Meulen, E. Norrby, W. Plowright, R. Rott, and W. H. Wunner, Intervirology 10, 137–152 (1978).
38. Kunkel, T. A., Proc. Natl. Acad. Sci. USA 82, 488–492 (1985).
39. Lennon, J. L., and F. L. Black, J. Ped. 108, 671–676 (1986).
40. Mandecki, W., Proc. Natl. Acad. Sci. USA 83, 7177–7181 (1982).
41. Mandecki, W., Proc. Natl. Acad. Sci. USA 83, 7177–7181 (1986).
42. Maniatis, T., E. F. Fritsch, and J. Sambrook, Molecular Cloning, Cold Spring Harbor Laboratory, N.Y. 545 pages (1982).
43. Maniatis, T., E. F. Fritsch, and J. Sambrook, Molecular Cloning, Cold Spring Harbor Laboratory, N.Y. 545 pages (1986).
44. Merz, D. C., A. Schied, and P. Choppin, J. Exp. Med. 151, 275–288 (1980).
45. Moura, R. A., and J. Warren, J. Bact. 82, 702–705 (1961).
46. Norrby, E., and Y. Gollmar, Infect. Immnun. 11, 231–239 (1975).
47. Norrby, E., G. Enders-Ruckle, and V. ter Meulen, J. Infect. Dis. 132, 262–269 (1975).
48. Norrby, E., S. N. Chen, T. Togashi, H. Shesberadaran, and K. P. Johnson, Archives of Virology 71, 1–11 (1982).
49. Norrby, E., and M. N. Oxman, In Fields Virology 2nd Ed., B. N. Fields and D. M. Knipe, eds. (Raven Press, N.Y.) pp. 1013–1044 (1990).
50. Novick, S. L. and D. Hoekstra, Proc. Natl. Acad. Sci. USA 85, 7433–7437 (1988).
51. Orvell, C., and E. Norrby, J. Gen. Virol. 50, 231–245 (1980).
52. Panicali, D., and E. Paoletti, Proc. Natl. Acad. Sci. USA 79, 4927–4931 (1982).
53. Paterson, R. G., and R. A. Lamb, Cell 48, 441–452 (1987).
54. Perkus, M. E., A. Piccini, B. R. Lipinskas, and E. Paoletti, Science 229, 981–984 (1985).
55. Perkus, M. E., K. Limbach, and E. Paoletti, J. Virol. 63, 3829–3836 (1989).
56. Perkus, M. E., S. J. Goebel, S. W. Davis, G. P Johnson, K. Limbach, E. K. Norton, and E. Paoletti, Virology 179, 276–286 (1990).
57. Phillips, T. R., J. L. Jensen, M. J. Rubino, W. C. Yang, and R. D. Schultz, Can. J. Vet. Res. 53, 154–160 (1989).
58. Piccini, A., M. E. Perkus, and E. Paoletti, In Methods in Enzymology, Vol. 153, eds. Wu, R., and Grossman, L., (Academic Press) pp. 545–563 (1987).
59. Preblud, S. R., and S. L. Katz, In Vaccines, eds. S.A. Plotkin and E. A. Mortimer, (W. B. Saunders Co.) pp. 182–222 (1988).
60. Richardson, C. D., A. Berkovich, S. Rozenblatt, and W. Bellini, J. Virol. 54, 186–193 (1985).

61. Richardson, C., D. Hull, P. Greer, K. Hasel, A. Berkovich, G. Englund, W. Bellini, B. Rima, and R. Lazzarini, Virology 155, 508–523 (1986).
62. Roberts, J. A., J. Immunol. 94, 622–628 (1965).
63. Rosel, J. L., P. L. Earl, J. P. Weir, and B. looss, J. Virol. 60, 436–449 (1986).
64. Sanger, F., S. Nicklen, and A. R. Coulson, Proc. Natl. Acad. Sci. USA 74, 5463–5467 (1977).
65. Shapira, S. K., J. Chou, F. V. Richaud, and M. J. Casadaban, Gene 25, 71–82 (1983)
66. Spehner, D., R. Drillien, and J. P. Lecocq, J. Virol. 64, 527–533 (1990).
67. Stephenson, J. R. and V. ter Meulen, Proc. Nat. Acad. Sci. USA 76, 6601–6605 (1979).
68. Tabor, S., and C. C. Richardson, Proc. Natl. Acad. Sci. USA 84, 4767–4771 (1987).
69. Taylor, J., R. Weinberg, Y. kawaoka, R. G. Webster, and E. Paoletti, Vaccine 6, 504–508 (1988a).
70. Taylor, J., R. Weinberg, B. Languet, P. Desmettre, and E. Paoletti, Vaccine 6, 497–503 (1988b).
71. Taylor, J., C. Edbauer, A. Rey-Senelonge, J. F. Bouquet, E. Norton, S. Goebel, P. Desmettre, and E. Paoletti, J. Virol. 64, 1441–1450 (1990).
72. Taylor, J., S. Pincus, J. Tartaglia, C. Richardson, G. Alkhatib, D. Briedis, M. Appel, E. Norton, and E. Paoletti, J. Virol. 65, 4263–4272 (1991).
73. Tizard, I., J. Am. Vet. Med. Assoc. 196, 1851–1858 (1990).
74. Vialard, J., M. Lalumiere, T. Vernet, D. Briedis, G. Alkhatib, D. Henning, D. Levin, and C. Richardson, J. Virol. 64, 37–50 (1990).
75. Warren, J., M. K. Nadel, E. Slater, and S. J. Millian, Amer. J. Vet. Res. 21, 111–119 (1960).
76. Wild, T. F., E. Malvoisin, and R. Buckland, J. Gen. Virol. 72, 439–442 (1991).
77. Wild, F., P. Giraudon, D. Spehner, R. Drillien, and J-P. Lecocq, Vaccine 8, 441–442 (1990).
78. Yuen, L., and B. Moss, Proc. Natl. Acad. Sci. USA 84, 6417–6421 (1987).

What is claimed is:

1. A recombinant vaccinia virus wherein the open reading frames from the thymidine kinase gene, the hemorrhagic region, the A type inclusion body region, the hemagglutinin gene, the host range gene region, and the large subunit, ribonucleotide reductase have been deleted therefrom and, comprising DNA from Morbillivirus coding for at least one glycoprotein, and a promoter for expressing the DNA, in a nonessential region of the vaccinia genome.

2. A recombinant vaccinia virus wherein regions C7L–K1L, J2R, B13R+B14R, A26L, A56R and I4L have been deleted therefrom and, comprising DNA from coding for at least one Morbillivirus glycoprotein, and a promoter for expressing said DNA, in a nonessential region of the vaccinia genome.

3. A recombinant vaccinia virus as in claim 1 or 2 wherein said DNA codes for Morbillivirus hemagglutinin glycoprotein.

4. A recombinant vaccinia virus as in claim 1 or 2 wherein said DNA codes for Morbillivirus fusion glycoprotein.

5. A recombinant vaccinia virus as in claim 1 or 2 wherein said DNA codes for Morbillivirus hemagglutinin glycoprotein and fusion glycoprotein.

6. A recombinant vaccinia virus as in claim 1 or 2 wherein said DNA is expressed in a host by the production of at least one of Morbillivirus fusion and hemagglutinin glycoprotein.

7. A recombinant vaccinia virus as in claim 6 wherein said Morbillivirus glycoprotein is Morbillivirus hemagglutinin glycoprotein.

8. A recombinant vaccinia virus as in claim 6 wherein said Morbillivirus glycoprotein is Morbillivirus fusion glycoprotein.

9. A recombinant vaccinia virus as in claim 6 wherein said DNA is expressed in a host by the production of the Morbillivirus fusion and hemagglutinin glycoproteins.

10. A recombinant vaccinia virus as in claim 1 or 2 wherein said DNA is introduced into said vaccinia virus by recombination.

11. A recombinant vaccinia virus as claimed in 1 or 2 wherein the DNA from Morbillivirus is under the transcriptional control of an H6 promoter and in a nonessential region of the vaccinia virus genome.

12. A immunological composition for inducing an antigenic response in a host animal inoculated with said immunologioal composition, said immunological composition comprising a carrier and a recombinant vaccinia as claimed in claim 1 or 2.

13. An immunological composition as in claim 12 wherein said DNA codes for and expresses Morbillivirus hemagglutinin glycoprotein.

14. An immunological composition as in claim 12 wherein said DNA codes for and expresses Morbillivirus fusion glycoprotein.

15. An immunological composition as in claim 12 wherein said DNA codes for and expresses Morbillivirus fusion and hemagglutinin glycoproteins.

16. An immunological composition as in claim 12 wherein said DNA is introduced into said vaccinia virus by recombination.

17. A method for inducing an immunological response in a host against a Morbillivirus, which method comprises administering to the host a recombinant vaccinia virus as claimed in claim 1.

18. A method as in claim 17 wherein said DNA codes for Morbillivirus fusion and hemagglutinin glycoproteins.

19. A method as in claim 17 wherein said DNA codes for Morbillivirus hemagglutinin glycoprotein.

20. A method as in claim 17 wherein said DNA codes for Morbillivirus fusion glycoprotein.

21. A method for protecting a dog against canine distemper which method comprises inoculating the dog with a recombinant vaccinia virus containing therein DNA from a Morbillivirus in a nonessential region of the vaccinia genome; and said DNA codes for measles virus hemagglutinin glycoprotein.

22. A method for protecting a dog against canine distemper, which method comprises inoculating the dog with a recombinant avipox virus containing therein DNA from Morbillivirus in a nonessential region of the avipox virus genome and a promoter for expressing the DNA; wherein said DNA codes for measles virus hemagglutinin glycoprotein.

23. The method of claim 22 wherein the avipox virus is a canarypox virus.

24. A recombinant ALVAC virus comprising DNA from Morbillivirus coding for at least one glycoprotein, and a promoter for expressing the DNA, in a nonessential region of the ALVAC genome.

25. A recombinant ALVAC virus as in claim 24 wherein said DNA codes for Morbillivirus hemagglutinin glycoprotein.

26. A recombinant ALVAC virus as in claim 24 wherein said DNA codes for Morbillivirus fusion glycoprotein.

27. A recombinant ALVAC virus as in claim 24 wherein said DNA codes for Morbillivirus hemagglutinin glycoprotein and fusion glycoprotein.

28. A recombinant ALVAC virus as in claim 24 wherein said DNA is expressed in a host by the production of at least one of measles virus fusion and hemagglutinin glycoprotein.

29. A recombinant ALVAC virus as in claim 28 wherein said measles virus glycoprotein is measles virus hemagglutinin glycoprotein.

30. A recombinant ALVAC virus as in claim 28 wherein said measles virus glycoprotein is measles virus fusion glycoprotein.

31. A recombinant ALVAC virus as in claim 28 wherein said DNA is expressed in a host by the production of the measles virus fusion and hemagglutinin glycoproteins.

32. A recombinant ALVAC virus as in claim 24 wherein said DNA is introduced into said ALVAC virus by recombination.

33. An immunological composition for inducing an antigenic response in a host animal inoculated with said vaccine, said vaccine comprising a carrier and recombinant ALVAC as claimed in claim 24.

34. An immunological composition as in claim 33 wherein said DNA codes for expresses measles virus hemagglutinin glycoprotein.

35. An immunological composition as in claim 33 wherein said DNA codes for and expresses measles virus fusion glycoprotein.

36. An immunological composition as in claim 33 wherein said DNA codes for and expresses the measles virus fusion and hemagglutinin glycoproteins.

37. An immunological composition as in claim 33 wherein said DNA is introduced into said ALVAC virus by recombination.

38. A method for inducing an immunological response in a host against a Morbillivirus, which method comprises administering to the host a recombinant ALVAC virus as claimed in claim 24 or 28.

39. A method as in claim 38 wherein said DNA codes for measles virus fusion and hemagglutinin glycoproteins.

40. A method as in claim 38 wherein said DNA codes for measles virus hemagglutinin glycoprotein.

41. A method as in claim 38 wherein said DNA codes for measles virus fusion glycoprotein.

42. A method for expressing a gene product in vitro comprising infecting a cell with a recombinant as claimed in claim 1, 2 or 24, transforming cell with the expression vector, cultivating the transformed cell under conditions which allow expression of the gene product and further purifying the product.

* * * * *

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 128 base pairs
( B ) TYPE: nucleic acid
( C ) STRANDEDNESS: single
( D ) TOPOLOGY: linear ( x i ) SEQUENCE DESCRIPTION: SEQ ID NO:1:

```
AGCTTCTTTA TTCTATACTT AAAAAGTGAA AATAAATACA AAGGTTCTTG AGGGTTGTGT        60

TAAATTGAAA GCGAGAAATA ATCATAAATT ATTTCATTAT CGCGATATCC GTTAAGTTTG       120

TATCGTAC                                                                128
```

( 2 ) INFORMATION FOR SEQ ID NO:2:

( i ) SEQUENCE CHARACTERISTICS:
( A ) LENGTH: 128 base pairs
( B ) TYPE: nucleic acid
( C ) STRANDEDNESS: single
( D ) TOPOLOGY: linear ( x i ) SEQUENCE DESCRIPTION: SEQ ID NO:2:

```
TCGAGTACGA TACAAACTTA ACGGATATCG CGATAATGAA ATAATTTATG ATTATTCTC        60

GCTTTCAATT TAACACAACC CTCAAGAACC TTTGTATTTA TTTTCACTTT TTAAGTATAG      120

AATAAAGA                                                                128
```

( 2 ) INFORMATION FOR SEQ ID NO:3:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:3:

```
ATTATTTTA TAAGCTTGGA TCCCTCGAGG GTACCCCGG GGAGCTCGAA TTCT              54
```

( 2 ) INFORMATION FOR SEQ ID NO:4:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AGAATTCGAG CTCCCCGGGG GTACCTCGA GGGATCCAAG CTTATAAAAA TAAT    54

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGGAAGATGG AACCAATCGC AGATAG    26

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AATTCTATCT GCGATTGGGG TTCCATCTTC CC    32

( 2 ) INFORMATION FOR SEQ ID NO:7:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ATATCCGTTA AGTTTGTATC GTAATGTCAC CACAACGAGA CCGGAT    46

( 2 ) INFORMATION FOR SEQ ID NO:8:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CCTAAAGCCT GATCTTACGG GAACATCAAA ATCCTATGTA AGGTCGCTCT GATTTTATC    60

GGCCGA    66

( 2 ) INFORMATION FOR SEQ ID NO:9:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AGCTTCGGCC GATAAAATC AGAGCGACCT TACATAGGAT TTTGATGTTC CCGTAAGATC    60

AGGCTTTAGG                                                                                          70

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GGGATGGGTC TCAAGGTGAA CGTCTCTGCC ATATTC                                                             36

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

ATGGCAGAGA CGTTCACCTT GAGACCCATC CC                                                                 32

( 2 ) INFORMATION FOR SEQ ID NO:12:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TATCCGTTAA GTTTGTATGG TAATGGGTCT CAAGGTGAAC GTCT                                                    44

( 2 ) INFORMATION FOR SEQ ID NO:13:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AATAAATCAC TTTTTATACT AATTCTTTAT TCTATACTTA AAAAGT                                                  46

( 2 ) INFORMATION FOR SEQ ID NO:14:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GACTATCCTA CTTCCCTTGG GATGGGGGTT ATCTTTGTA                                                          39

( 2 ) INFORMATION FOR SEQ ID NO:15:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

ACTCTCAAAA GCTTCCCGGG AATTCTAGCT AGCTAGTTTT TATAAA                                                  46

( 2 ) INFORMATION FOR SEQ ID NO:16:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GATCTTTATA AAAACTAGCT AGCTAGAATT CCCGGGAAGC TTTTGAGAGT    50

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

TAATTAACTA GCTACCCGGG    20

( 2 ) INFORMATION FOR SEQ ID NO:18:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AATTCCCGGG TAGCTAGTTA ATTACATG    28

( 2 ) INFORMATION FOR SEQ ID NO:19:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AGCTTCCCGG GTAAGTAATA CGTCAAGGAG AAAACGAAAC GATCTGTAGT TAGCGGCCGC    60

CTAATTAACT AAT    73

( 2 ) INFORMATION FOR SEQ ID NO:20:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

ATTAGTTAAT TAGGCGGCCG CTAACTACAG ATCGTTTCGT TTTCTCCTTG ACGTATTACT    60

TACCCGGGA    69

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
TTAGTTAATT AGGCGGCCGC                                                    20
```

( 2 ) INFORMATION FOR SEQ ID NO:22:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
CGATTACTAT GAAGGATCCG TT                                                 22
```

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
AACGGATCCT TCATAGTAAT                                                    20
```

( 2 ) INFORMATION FOR SEQ ID NO:24:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
CGATTACTAG ATCTGAGCTC CCCGGGCTCG AGGGATCCGT T                            41
```

( 2 ) INFORMATION FOR SEQ ID NO:25:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
AACGGATCCC TCGAGCCCGG GGAGCTCAGA TCTAGTAAT                               39
```

( 2 ) INFORMATION FOR SEQ ID NO:26:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
GATCCGAATT CTAGCT                                                        16
```

( 2 ) INFORMATION FOR SEQ ID NO:27:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
AGCTAGAATT CG                                                            12
```

( 2 ) INFORMATION FOR SEQ ID NO:28:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

```
TATGAGTAAC TTAACTCTTT TGTTAATTAA AAGTATATTC AAAAAATAAG TTATATAAAT      60

AGATCTGAAT TCGTT                                                      75
```

( 2 ) INFORMATION FOR SEQ ID NO:29:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
AACGAATTCA GATCTATTTA TATAACTTAT TTTTGAATA TACTTTTAAT TAACAAAAGA       60

GTTAAGTTAC TCA                                                        73
```

( 2 ) INFORMATION FOR SEQ ID NO:30:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
AAAATGGGCG TGGATTGTTA ACTTATATA ACTTATTTT TGAATATAC                    49
```

( 2 ) INFORMATION FOR SEQ ID NO:31:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
ACACGAATGA TTTCTAAAG TATTGGAAA GTTTATAGG TAGTTGATAG AACAAAATAC         60

ATAATTT                                                               67
```

( 2 ) INFORMATION FOR SEQ ID NO:32:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
TCTATCAACT ACCTATAAAA CTTTCCAAAT ACTTTAGAAA ATCATTCGTG T               51
```

( 2 ) INFORMATION FOR SEQ ID NO:33:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

TGTAAAAATA AATCACTTTT TATACTAAGA TCTCCCGGGC TGCAGC    46

( 2 ) INFORMATION FOR SEQ ID NO:34:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GGCCGCTGCA GCCCGGGAGA TCTTAGTATA AAAAGTGATT TATTTTACA AAATTATGTA    60

TTTTGT    66

( 2 ) INFORMATION FOR SEQ ID NO:35:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

TTTCTGTATA TTTGCACCAA TTTAGATCTT ACTCAAAATA TGTAACAATA    50

( 2 ) INFORMATION FOR SEQ ID NO:36:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

TGTCATTTAA CACTATACTC ATATTAATAA AAATAATATT TATT    44

( 2 ) INFORMATION FOR SEQ ID NO:37:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GATCCTGAGT ACTTTGTAAT ATAATGATAT ATATTTCAC TTTATCTCAT TTGAGAATAA    60

AAAGATCTTA GG    72

( 2 ) INFORMATION FOR SEQ ID NO:38:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

AATTCCTAAG ATCTTTTAT TCTCAAATGA GATAAAGTGA AAATATATAT CATTATATTA    60

CAAAGTACTC AG    72

( 2 ) INFORMATION FOR SEQ ID NO:39:

( i ) SEQUENCE CHARACTERISTICS:
        ( A ) LENGTH: 72 base pairs

-continued (B) TYPE: nucleic acid
    (C) STRANDEDNESS: single
    (D) TOPOLOGY: linear ( x i ) SEQUENCE DESCRIPTION: SEQ ID NO:39:

GATCCAGATC TCCCGGGAAA AAAATTATTT AACTTTTCAT TAATAGGGAT TTGACGTATG    60

TAGCGTACTA GG    72

( 2 ) INFORMATION FOR SEQ ID NO:40:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

AATTCCTAGT ACGCATCATA CGTCAAATCC CTATTAATGA AAAGTTAAAT AATTTTTTC    60

CCGGGAGATC TG    72

( 2 ) INFORMATION FOR SEQ ID NO:41:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

TATCCGTTAA GTTTGTATCG TAATGGGTCT CAAGGTGAAC GTCT    44